(12) United States Patent
Gu et al.

(10) Patent No.: US 7,605,257 B2
(45) Date of Patent: Oct. 20, 2009

(54) PROCESSES FOR PREPARING WATER-SOLUBLE POLYETHYLENE GLYCOL CONJUGATES OF MACROLIDE IMMUNOSUPPRESSANTS

(75) Inventors: Jianxin Gu, River Edge, NJ (US); Mark Ruppen, Garnerville, NY (US); Tianmin Zhu, Monroe, NY (US); Mahdi Fawzi, Morristown, NJ (US)

(73) Assignee: Wyeth, Madison, NJ (US)

( * ) Notice: Subject to any disclaimer, the term of this patent is extended or adjusted under 35 U.S.C. 154(b) by 354 days.

(21) Appl. No.: 11/713,973

(22) Filed: Mar. 5, 2007

(65) Prior Publication Data

US 2007/0212371 A1 Sep. 13, 2007

Related U.S. Application Data

(60) Provisional application No. 60/779,939, filed on Mar. 7, 2006.

(51) Int. Cl.
*C07D 498/18* (2006.01)
(52) U.S. Cl. ..................................... 540/456
(58) Field of Classification Search ................ 540/456
See application file for complete search history.

(56) References Cited

U.S. PATENT DOCUMENTS

| | | | |
|---|---|---|---|
| 5,362,718 | A | 11/1994 | Skotnicki et al. |
| 5,780,462 | A | 7/1998 | Lee et al. |
| 5,955,457 | A | 9/1999 | Lee et al. |
| 6,277,983 | B1 | 8/2001 | Shaw et al. |
| 6,331,547 | B1 | 12/2001 | Zhu et al. |
| 6,432,973 | B1 | 8/2002 | Zhu et al. |
| 6,440,990 | B1 | 8/2002 | Cottens et al. |
| 2002/0055518 | A1 | 5/2002 | Zhu |
| 2005/0234087 | A1 | 10/2005 | Gu et al. |
| 2005/0234234 | A1 | 10/2005 | Gu et al. |

FOREIGN PATENT DOCUMENTS

| | | |
|---|---|---|
| WO | WO-99/03860 | 1/1999 |
| WO | WO 2005/105812 | 11/2005 |

OTHER PUBLICATIONS

Lopez-Pelegrin, Soluble Polymer-Supported Chemoenzymatic Synthesis of the C21-C27 Fragment of the Bryostatins, J. Org. Chem., vol. 65, No. 25, pp. 8527-8531, (Dec. 2000).
Uyama Hiroshi et al, Immobilized Lipase Showing High Catalytic Activity Toward Enzymic Ring-Opening Polymerization of Macrolides, Chemisry Letters, Chemical Society of Japan, vol. 2, pp. 107-108, (1996).
Rosen et al., "Natural Products as Probes of Cellular Function: Studies of Immunophilins", Angew. Chem. Int. Ed. Engl., 31:384-400 (Apr. 1992).
Yatscoff et al., "Rapamycin: Distribution, Pharmacokinetics, and Therapeutic Range Investigations", Ther. Drug. Monit., 17:666-671 (Dec. 1995).
Greenwald et al., "Effective Drug Delivery by PEGylated Drug Conjugates", Advanced Drug Delivery Rev., 55:217-250 (Feb. 2003).
Pasut et al., "Protein, Peptide and Non-Peptide Drug PEGylation for Therapeutic Application", Expert Opin. Ther. Patents, 14:859-894 (Jun. 1, 2004).
First Official Action in counterpart Pakistan application, pp. 3, (2008).

*Primary Examiner*—Bruck Kifle
(74) *Attorney, Agent, or Firm*—David A. Rubin, Esq.; Howson & Howson LLP

(57) ABSTRACT

Processes are described for preparing 42-pegylated rapamycins including reacting a rapamycin with an acylating agent in the presence of a lipase to form an acylated rapamycin and reacting the acylated rapamycin with a methoxy poly(ethylene glycol) derivative in the presence of a base. Also described are processes for preparing 32-pegylated tacrolimus and/or ascomycin using these steps.

23 Claims, No Drawings

PROCESSES FOR PREPARING WATER-SOLUBLE POLYETHYLENE GLYCOL CONJUGATES OF MACROLIDE IMMUNOSUPPRESSANTS

CROSS-REFERENCE TO RELATED APPLICATIONS

This application claims the benefit of the priority of U.S. Provisional Patent Application No. 60/779,939, filed Mar. 7, 2006.

BACKGROUND OF THE INVENTION

This invention relates to processes for preparing water soluble poly(ethylene glycol) conjugates of macrolide immunosuppressants sirolimus (rapamycin), everolimus, temsirolimus (CCI-779), tacrolimus (FK506) and ascomycin (FK520).

Rapamycin (1), tacrolimus (FK506, 2) and ascomycin (FK520, 3) are structurally similar macrocyclic polyketides and all are potent immunosuppressants that interact with the same intracellular receptors, but have different modes of action, suppressing T-cell activation at different stages (Rosen et al., "Natural products as probes of cellular function: studies of immunophilins" Angew. Chem. Int. Ed. Engl. 1992, 31, 384-400). These macrolides have antimicrobial activity and are also effective in animal models of autoimmune diseases including experimental allergic encephalomyelitis, arthritis, animal models of diabetes, the MRL/lpr mouse model of SLE, hyperproliferative ski diseases, and uveoretinitis.

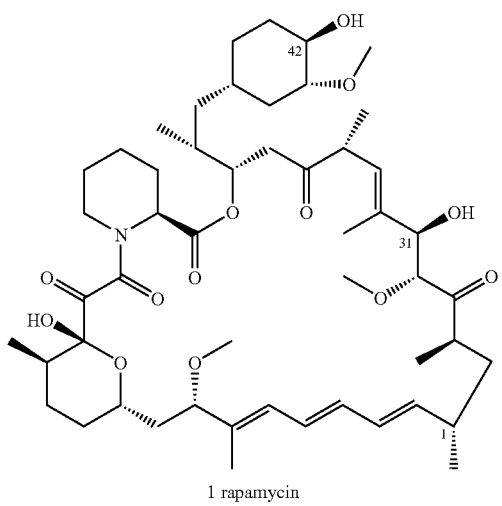

1 rapamycin

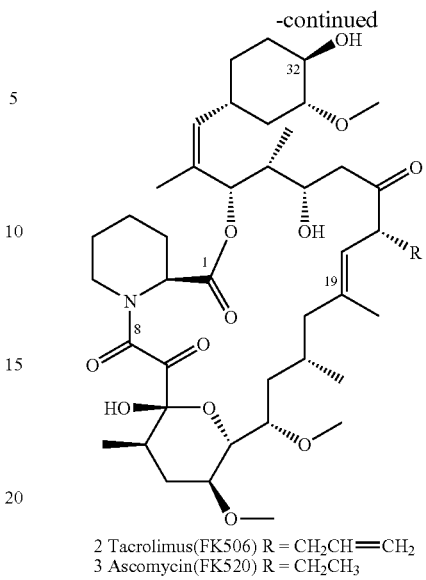

2 Tacrolimus(FK506) R = $CH_2CH=CH_2$
3 Ascomycin(FK520) R = $CH_2CH_3$

Rapamycin and tacrolimus have been approved for preventing transplantation rejection. However, both compounds share similar problems in formulating the compositions due to their very limited aqueous solubility. For example, tacrolimus has a solubility of 12 μg/mL in water. Such a low solubility requires a rather complicated formulation. For instance, 200 mg/mL of hydrogenated polyoxy 60 castor oil (HCO-60) and 80% (v/v) absolute alcohol are required as the solubilizing aid for dissolving 5 mg of tacrolimus for intravenous injections. Rapamycin has a solubility of about 2.6 μg/mL in water and low oral bioavailability (<15%) (Yatscoff et al., "Rapamycin: distribution, pharmacokinetics, and therapeutic range investigations" Ther. Drug Monit. 1995, 17, 666-671). These characteristics have limited rapamycin's clinical applications other than low-dosage treatment such as immunosuppression, despite it is also a potent inhibitor of tumor growth with a typical $IC_{50}<50$ nm against various solid tumors.

Polyethylene glycol (PEG) and methoxy polyethylene glycol (mPEG) are linear or branched, neutral polymers available in a variety of molecular weights with low polydispersities ($M_w/M_n<1.05$). These water/organic solvent soluble, non-toxic polymers have been found useful in biological and pharmaceutical applications. One such application is the binding of these polymers with the non or sparingly water-soluble small molecule therapeutics to make water soluble PEG-drug conjugates, termed PEGylation. Pegylation of organic molecules has been reported to enhance aqueous solubility of the organic molecule and to confer other beneficial properties such as improved plasma half-life, improved biological distribution, and reduced toxicity (Greenwald et al., "Effective drug delivery by PEGylated drug conjugates", Advanced Drug Delivery Rev. 2003, 55, 217-250; Pasut et al., "Protein, peptide and non-peptide drug PEGylation for therapeutic application", Expert Opin. Ther. Patents 2004, 14, 859-894).

The lipase-catalyzed acetylation of rapamycin has been discussed in US Patent Application Publication No. US-2005/0234234, which is hereby incorporated by reference. This enzymatic process gives rapamycin 42-ester derivatives regiospecifically from rapamycin with excellent yield under mild condition.

The preparation of PEG conjugates of rapamycin or its derivatives has been described in U.S. Pat. Nos. 5,955,457; 5,780,462; 6,432,973 and 6,331,547. The preparation of hydroxyester of rapamycin CCI-779, from which the pegylated CCI-779 was made from, was described in the U.S. Pat. No. 5,362,718, which is hereby incorporated by reference. These patents describe conjugates formed by chemically linking rapamycin or its derivatives to methoxy polyethylene glycol compounds such as a thiol derivative (mPEGSH) through an ester linkage. Solvent extraction and chromatography purification were thereby required to recover the desired PEG conjugate. By doing so, rapamycin 42-iodoacetate was prepared in a 55% yield after high performance liquid chromatography (HPLC) purification.

The preparation of the water soluble PEG-tacrolimus (FK-506) conjugate is discussed in International Patent Publication No. WO 99/03860 using a similar procedure. One major drawback of these procedures is the low selectivity of installation of the ester linkage due to the presence of multiple OH-functionalities in rapamycin/tacrolimus skeleton. Additionally, the use of aqueous sodium hydrogen carbonate as a base during pegylation generates several by-products, requiring multiple purification steps with low or moderate recovery yield.

The synthesis of everolimus is described in the U.S. Pat. No. 6,440,990 and the synthesis of PEG-everolimus (II) was described in the U.S. Pat. No. 6,331,547, which patents are hereby incorporated by reference.

What are needed in the art are alternate processes for preparing water soluble poly(ethylene glycol) conjugates of macrolide immunosuppressants.

SUMMARY OF THE INVENTION

In one aspect, processes are provided for preparing polyethylene glycol conjugates of immunosuppressive macrolides.

In another aspect, processes are provided for preparing polyethylene glycol conjugates of rapamycin, everolimus, temsirolimus, tacrolimus, and ascomycin.

Other aspects and advantages of the present invention are described further in the following detailed description of the preferred embodiments thereof.

DETAILED DESCRIPTION OF THE INVENTION

Novel, efficient processes for preparing polyethylene glycol conjugates with a rapamycin, including rapamycin, everolimus, temsirolimus; tacrolimus; or ascomycin in high yields are provided. The processes include simple isolation steps, which center on the installation of an ester linkage in these macrolides using lipases with complete regioselectivity and excellent yield of the pegylated conjugate.

As used herein, a polyethylene glycol, abbreviated (PEG), is a linear polymer having hydroxyl groups at each terminus:

HO—(CH$_2$CH$_2$O)$_n$CH$_2$CH$_2$—OH

This formula can be represented as HO-PEG-OH, where it is understood that -PEG- represents the polymer backbone without the terminal groups:

—(CH$_2$CH$_2$O)$_n$CH$_2$CH$_2$—

A polyethylene glycol can also include mono-activated, alkyl-terminated polyethylene glycols, such as methoxy-PEG-OH (mPEGOH):

CH$_3$O(CH$_2$CH$_2$O)$_n$CH$_2$CH$_2$—OH in which one terminus is the inert methoxy group, while the other terminus is a hydroxyl group that is ready for chemical modification. In one embodiment, the activated mPEG's are methoxy-PEG-SH (mPEGSH):

CH$_3$O(CH$_2$CH$_2$O)$_n$CH$_2$CH$_2$—SH

In another embodiment, a polyethylene glycol can also include bis-activated, thiol-terminated polyethylene glycols, such as HS-PEG-SH (PEGSH):

HS—(CH$_2$CH$_2$O)$_n$CH$_2$CH$_2$—SH is also contemplated for such purposes.

Although polyethylene glycols vary substantially by molecular weight, polymers having molecular weights ranges from about 400 to about 30,000 are usually selected. In one example, polyethylene glycols of molecular weights of from about 1000 to about 30,000 are selected. In another example, polyethylene glycols of molecular weights of from about 2500 to 20,000 are selected. In a further example, polyethylene glycols of molecular weights of from about 5000 to about 20,000 are selected. One of skill in the art will readily understand that in these formulas, n is an integer, typically in the range of from 10 to 1000.

As defined herein, "a rapamycin" refers to rapamycin and to compounds which may be chemically or biologically modified as derivatives of the rapamycin nucleus, while still retaining biological activities. Accordingly, the term "a rapamycin" includes esters, ethers, carbonates, carbamates, oximes, hydrazones, and hydroxylamines of rapamycin, as well as rapamycins in which functional groups on the nucleus have been modified, for example through reduction or oxidation. The term "a rapamycin" also includes pharmaceutically acceptable salts of rapamycins, which are capable of forming such salts, either by virtue of containing an acidic or basic moiety.

In one embodiment, the esters and ethers of rapamycin are esters and ethers of the hydroxyl group at the 31-position of the rapamycin nucleus, esters and ethers of a hydroxyl group at the 27-position (following chemical reduction of the 27-ketone), esters and ethers of the hydroxyl group at the 42-position, particularly hydroxyalkyl, hydroxyalkenyl, hydroxyalkylaryl esters or ethers of hydroxyl group at the 42-position of the rapamycin. The oximes, hydrazones, and hydroxylamines are of a ketone of the rapamycin nucleus.

In other embodiments, 31-esters and ethers of rapamycin are described in the following patents: alkyl esters (U.S. Pat. No. 4,316,885); aminoalkyl esters (U.S. Pat. No. 4,650,803); fluorinated esters (U.S. Pat. No. 5,100,883); amide esters (U.S. Pat. No. 5,118,677); carbamate esters (U.S. Pat. Nos. 5,118,678; 5,441,967; 5,434,260; 5,480,988; 5,480,989; and 5,489,680); silyl ethers (U.S. Pat. No. 5,120,842); aminoesters (U.S. Pat. No. 5,130,307); acetals (U.S. Pat. No. 5,51,413); aminodiesters (U.S. Pat. No. 5,162,333); sulfonate and sulfate esters (U.S. Pat. No. 5,177,203); esters (U.S. Pat. No. 5,221,670); alkoxyesters (U.S. Pat. No. 5,233,036); O-aryl, -alkyl, -alkenyl, and -alkynyl ethers (U.S. Pat. No. 5,258,389); carbonate esters (U.S. Pat. No. 5,260,300); arylcarbonyl and alkoxycarbonyl carbamates (U.S. Pat. No. 5,262,423); carbamates (U.S. Pat. No. 5,302,584); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385,910); amino alkanoic esters (U.S. Pat. No. 5,389,639); phosphorylcarbamate esters (U.S. Pat. No. 5,391,730); amino carbamate esters (U.S. Pat. No. 5,463,048); hindered N-oxide esters (U.S. Pat. No. 5,491,231); biotin esters (U.S. Pat. No. 5,504, 091); and O-alkyl ethers (U.S. Pat. No. 5,665,772). The preparation of these esters and ethers is described in the patents listed above.

In still other embodiments, 27-esters and ethers of rapamycin are discussed in U.S. Pat. No. 5,256,790. The preparation of these esters and ethers is described in the patents listed above.

In still other embodiments, 42-hydroxyalkyl, 42-hydroxyalkenyl, 42-hydroxyalkylaryl ethers of the rapamycin are disclosed in U.S. Pat. Nos. 6,440,990; 5,665,772; and 5,258,389. 42-Hydroxyalkyl, 42-hydroxyalkenyl, 42-hydroxyalkylaryl esters of the rapamycin are disclosed in U.S. Pat. No. 5,362,718. The preparation of these esters and ethers is described in the patents listed above.

In one embodiment, the immunosuppressive macrolide contains a shikimic acid derived cyclohexyl region. In one example, the immunosuppressive macrolide is a rapamycin, tacrolimus or ascomycin.

In another embodiment, the immunosuppressive macrolide is a rapamycin and has the structure:

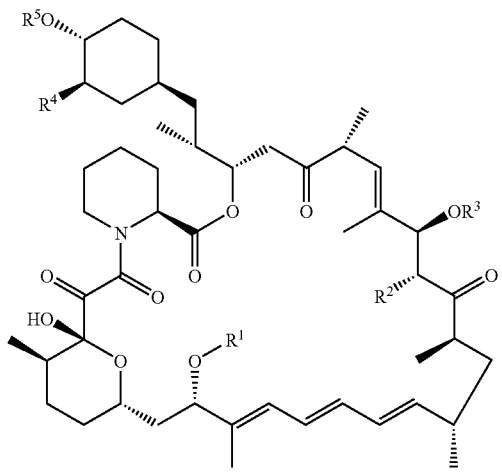

wherein, $R^1$ is selected from among H, and alkyl, alkenyl, aryl, and arylalkyl; $R^2$ is selected from among H, hydroxyl, and —O-alkyl; $R^3$ is H, alkyl, alkenyl, aryl, arylalkyl, and —C(O)$R^{31}$; $R^{31}$ is selected from among H, alkyl, alkenyl, aryl, and arylalkyl; $R^4$ is selected from among H, hydroxyl, and —O-alkyl; $R^5$ is selected from among H, hydroxyalkyl, hydroxyalkenyl, hydroxyaryl, hydroxyaralkyl, and —C(O)$R^{51}$; and $R^{51}$ is selected from among hydroxyalkyl, hydroxyalkenyl, hydroxyaryl, and hydroxyaralkyl.

Examples of "a rapamycin" include, without limitation, rapamycin (U.S. Pat. No. 3,929,992), 32-desmethylrapamycin, 32-desmethoxyrapamycin, 41-desmethylrapamycin, 41-desmethoxyrapamycin (International Patent Publication No. WO-2004/007709), 7,32-bis-desmethylrapamycin, proline-rapamycin, rapamycin 42-ester with 3-hydroxy-2-(hydroxymethyl)-2-methylpropionic acid (CCI-779, U.S. Pat. No. 5,362,718), and 42-O-(2-hydroxy)ethyl rapamycin (Everolimus, RAD001, U.S. Pat. No. 5,665,772).

The processes described herein thereby provide for preparing polyethylene glycol conjugates of immunosuppressive macrolides. The processes include reacting an acylating agent with an immunosuppressive macrolide having a shikimic acid derived cyclohexyl region in the presence of a lipase to form an acylated macrolide. The acylated macrolide is then reacted with a methoxy poly(ethylene glycol) derivative in the presence of a base. In one embodiment, the immunosuppressive macrolide is a rapamycin compound.

In one embodiment, a PEG-rapamycin conjugate has the following structure:

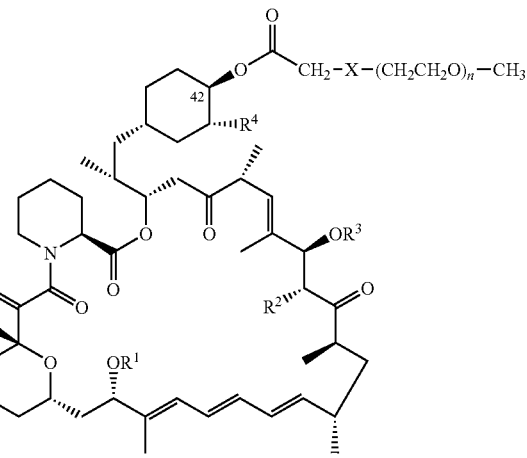

wherein, $R^1$ is selected from among H, and alkyl, alkenyl, aryl, and arylalkyl; $R^2$ is selected from among H, hydroxyl, and —O-alkyl; $R^3$ is H, alkyl, alkenyl, aryl, arylalkyl, or —C(O)$R^{31}$; $R^{31}$ is selected from among H, alkyl, alkenyl, aryl, and arylalkyl; $R^4$ is selected from among H, hydroxyl, and —O-alkyl; X is selected from among oxygen (—O—), —O-alkyl-O—, —O-alkenyl-O, —O-aryl-O—, —O-arylalkyl-O—, and —OC(O)$R_7$; $R_7$ is selected from among -alkyl-O—, -alkenyl-O—, -aryl-O—, and -arylalkyl-O—; n is an integer from 10 to 1000; and X is O or S.

In a further embodiment, a PEG-rapamycin conjugate has structure (I):

(I)

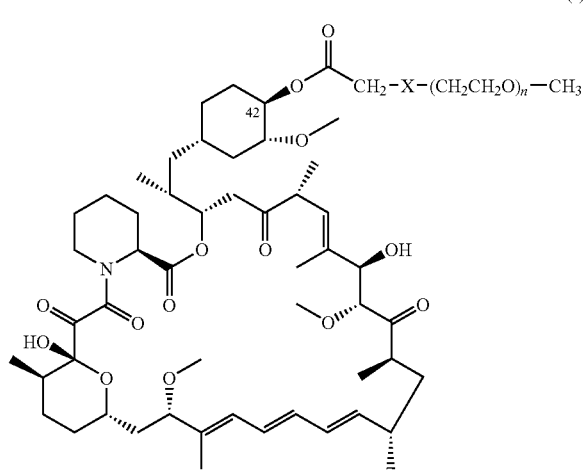

wherein, n is an integer from 10 to 1000; and X is O or S.

In another embodiment, a PEG-rapamycin conjugate has structure (II):

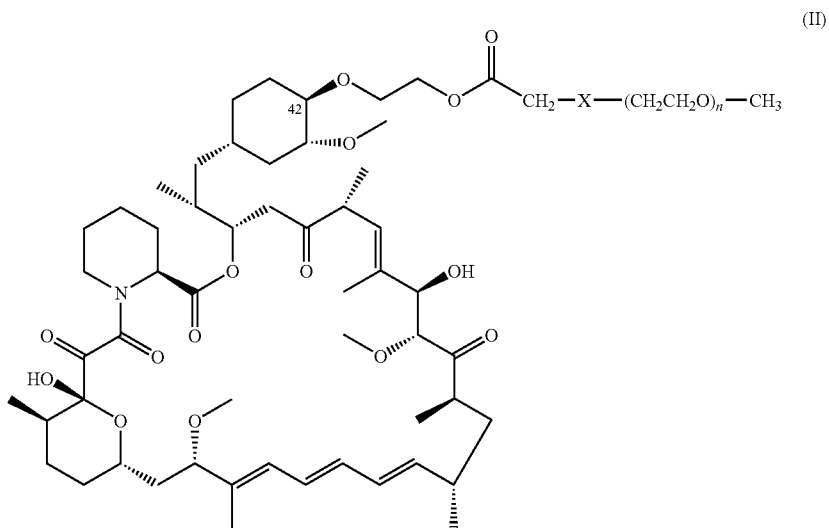
wherein, X and n are defined above.
In still another embodiment, a PEG-rapamycin conjugate has structure (III):
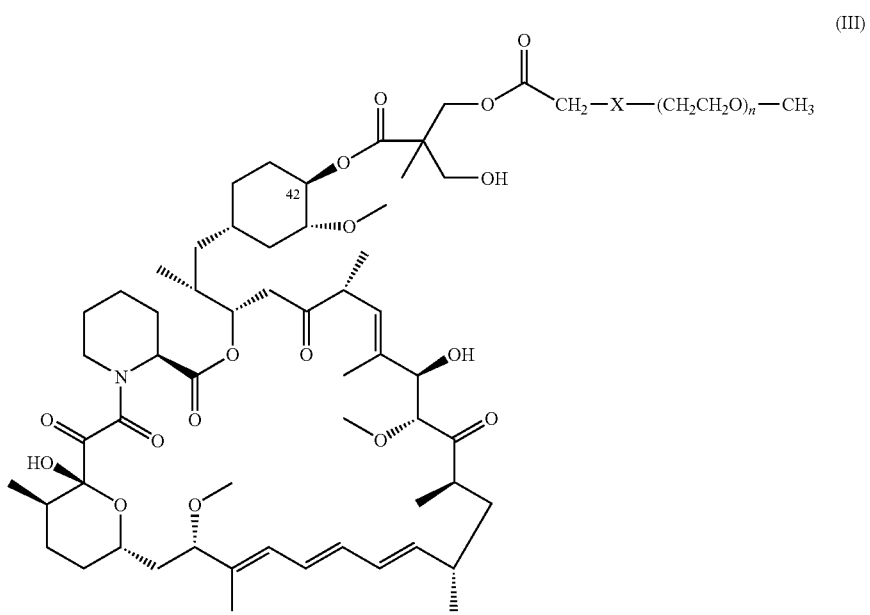
wherein, X and n are defined above.

In still another embodiment, a PEG-rapamycin conjugate has structure (IV):

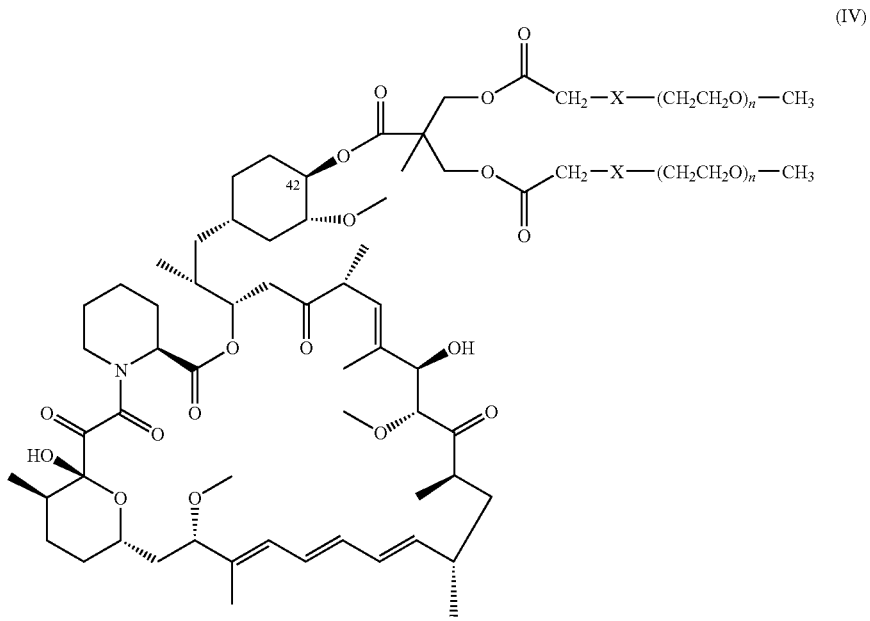

wherein, X and n are defined above.

The processes are also useful for preparing PEG conjugates with immunophilins other than the rapamycin compounds. The immunophilins contain a shikimic acid derived cyclohexyl region analogous to the 42-OH functionality of the rapamycin compounds, including, without limitation, FK-506 related natural products.

As used herein, the term "FK-506 related natural products" refers to compounds having the following core structure:

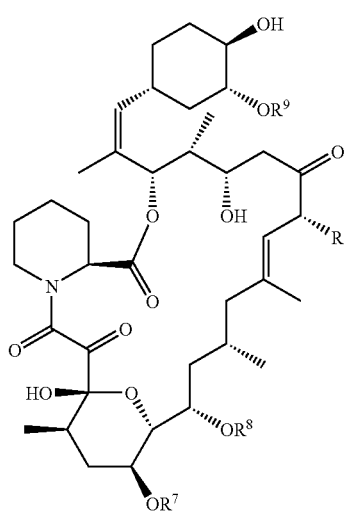

wherein, $R^7$, $R^8$, and $R^9$ are, independently, H or alkyl and R is ethyl or allyl. In one example, $R^7$, $R^8$, and $R^9$ are Me; and R is $CH_2CH=CH_2$. In another example, $R^7$, $R^8$, and $R^9$ are Me; and R is $CH_2CH_3$.

The term "alkyl" is used herein to refer to both straight- and branched-chain saturated aliphatic hydrocarbon groups having one to ten carbon atoms (e.g., $C_1$, $C_2$, $C_3$, $C_4$, $C_5$, $C_6$, $C_7$, $C_8$, $C_9$, or $C_{10}$), such as one to eight carbon atoms (e.g., $C_1$, $C_2$, $C_3$, $C_4$, $C_5$, $C_6$, $C_7$, or $C_8$), one to six carbon atoms (e.g., $C_1$, $C_2$, $C_3$, $C_4$, $C_5$, or $C_6$), or one or four carbon atoms (e.g., $C_1$, $C_2$, $C_3$, or $C_4$). The term "alkenyl" refers to both straight- and branched-chain alkyl groups with at least one carbon-carbon double bond and two to eight carbon atoms (e.g., $C_2$, $C_3$, $C_4$, $C_5$, $C_6$, $C_7$, or $C_8$), two to six carbon atoms (e.g., $C_2$, $C_3$, $C_4$, $C_5$, or $C_6$), or two to four carbon atoms (e.g., $C_2$, $C_3$, or $C_4$). The term "alkynyl" refers to both straight- and branched-chain alkyl groups with at least one carbon-carbon triple bond and two to eight carbon atoms (e.g., $C_2$, $C_3$, $C_4$, $C_5$, $C_6$, $C_7$, or $C_8$), two to six carbon atoms (e.g., $C_2$, $C_3$, $C_4$, $C_5$, or $C_6$), or two to four carbon atoms (e.g., $C_2$, $C_3$, or $C_4$).

The term "aryl" is used herein to refer to a carbocyclic aromatic system, which may be a single ring, or multiple aromatic rings fused or linked together as such that at least one part of the fused or linked rings forms the conjugated aromatic system. The aryl groups include, but are not limited to, phenyl, naphthyl, biphenyl, anthryl, tetrahydronaphthyl, phenanthryl, and indane.

The term "arylalkyl" refers to an alkyl group which is substituted by an aryl group. The alkyl group may be located at any point on the aryl group provided that the attachment constitutes a stable chemical bond.

The term "aralkyl" as used herein refers to an alkyl group having an aryl group attached to any carbon-atom on the alkyl group.

The terms "hydroxyalkyl", "hydroxyalkenyl", "hydroxyaryl", and "hydroxyaralkyl" refer to alkyl, alkenyl, aryl, and aralkyl groups as just described having a —OH group attached to any carbon-atom of the alkyl, alkenyl, aryl, or aralkyl group provided that the attachment constitutes a stable chemical bond.

The term "halogen" refers to Cl, Br, F, or I.

In one embodiment, the FK506 related natural product conjugate is PEG-tacrolimus has the structure of formula (V):

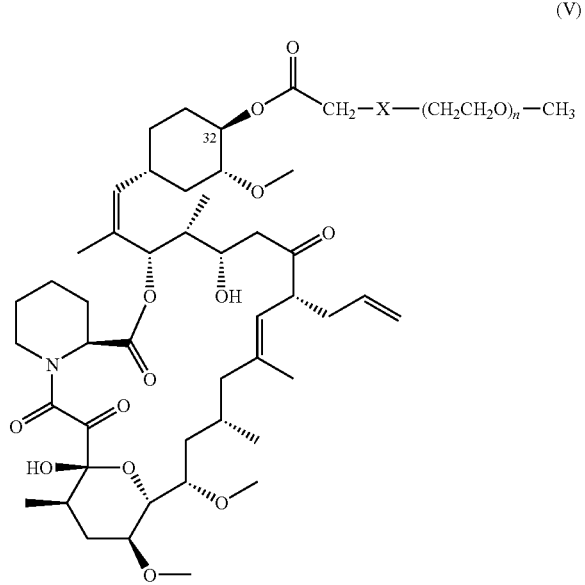
(V)
wherein, n is an integer from 10 to 1000; and X is O or S.
In another embodiment, the FK506 related natural product conjugate is PEG-ascomycin has the structure of formula (VI):
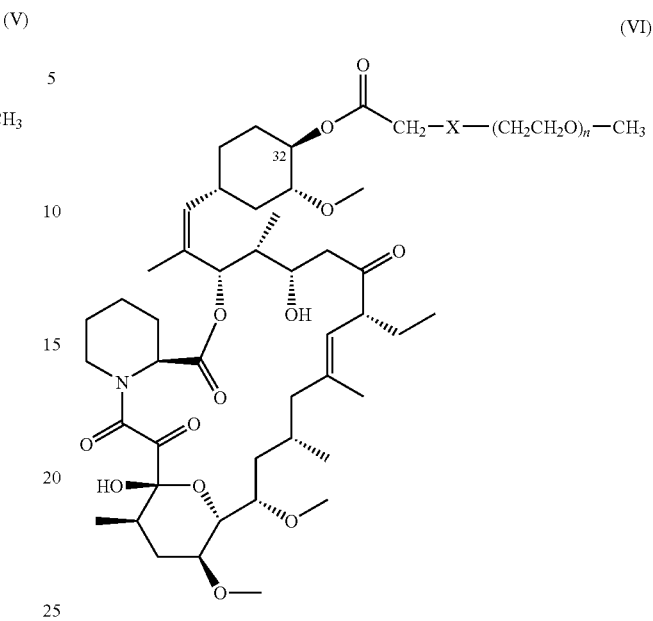
(VI)
wherein, n is an integer from 10 to 1000; and X is O or S.
Thus, in one embodiment, a process is provided for preparing a water soluble conjugate of formula I. See, Scheme 1.
Scheme 1
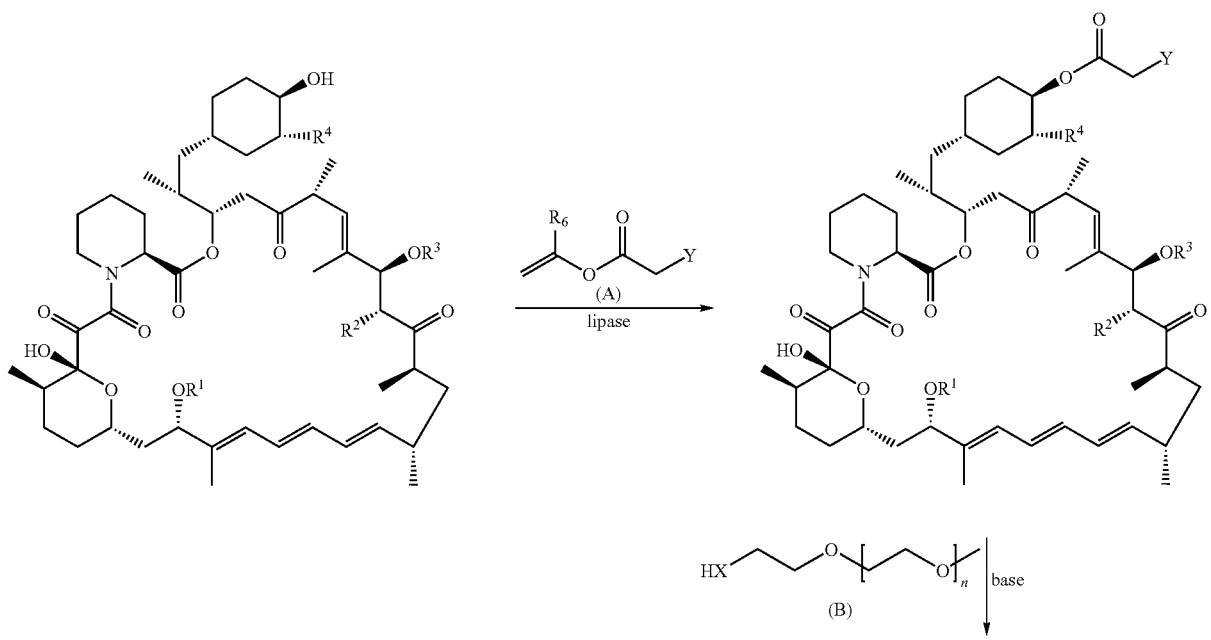

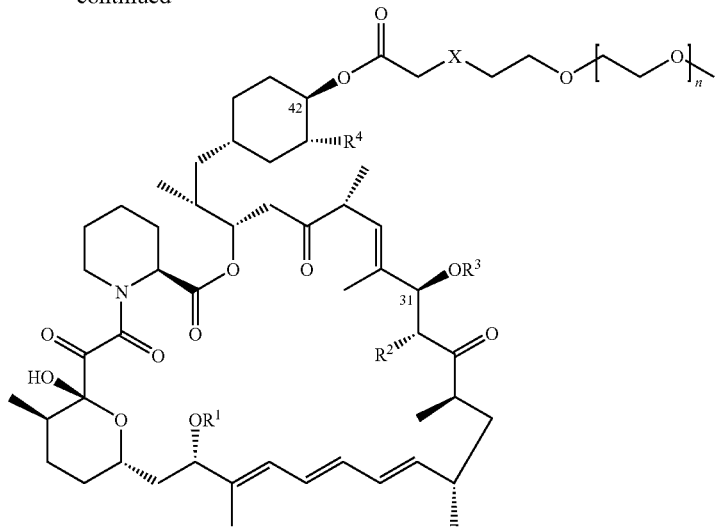
wherein $R^1$, $R^2$, $R^3$, $R^4$ are defined above.
In another embodiment, a process is provided for preparing a water soluble PEG-rapamycin conjugate represented by the formula (I) through a two-step sequence as outlined in Scheme 2.
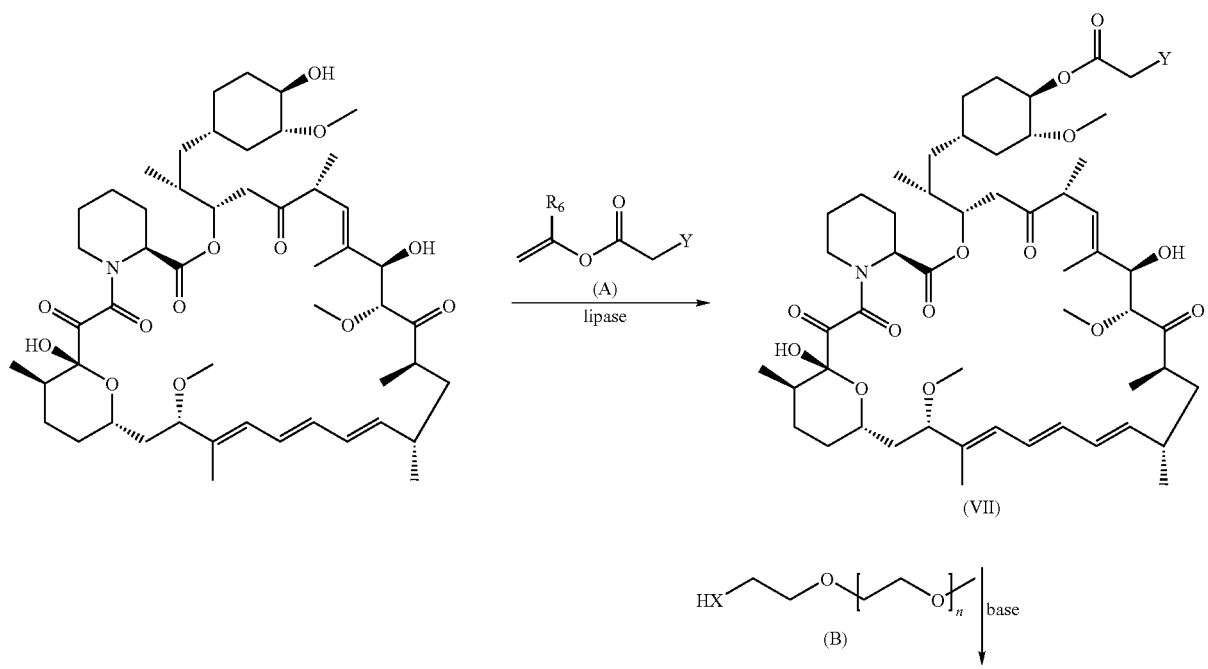

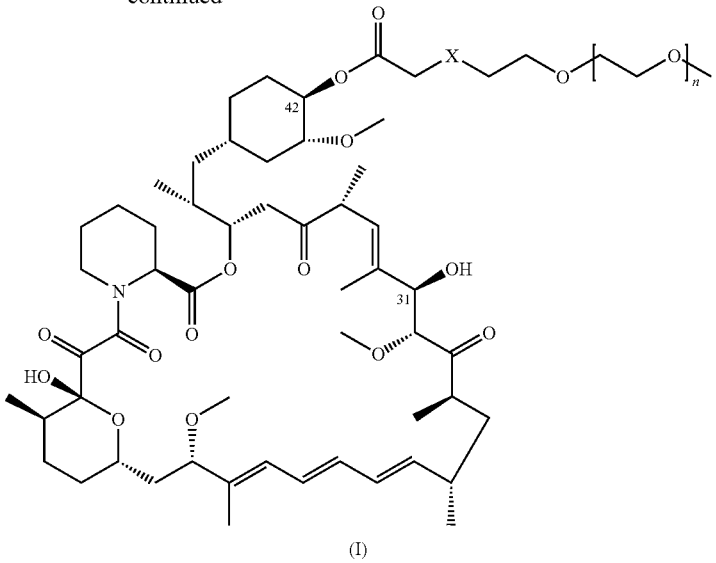

(I)

wherein, X is S or O; Y is a leaving group such as a halogen; and $R_6$ is H or methyl.

As can be seen from Schemes 1 and 2, the rapamycin conjugate is in the form of an ester wherein the methoxy polyethylene glycol is attached to rapamycin through an ester linker at position 42. In contrast to the methods in the art, the synthesis of this activated rapamycin 42-ester derivative as described herein is accomplished via a lipase-catalyzed acylation of rapamycin with an activated ester (A) having the following general formula:

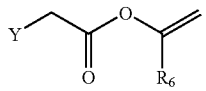

(A)

wherein, $R_6$ is H or $CH_3$; and Y is a leaving group.

Examples of leaving groups include, but are not limited to, halogens and sulfonates such as methanesulfonate (mesylate, MsO) and p-toluenesulfonate (tosylate, TsO). In one embodiment, the leaving group is a halogen such as I, Br, or Cl. In another embodiment, the activated ester is a vinyl ester of 2-haloacetic acid ($R_6$=H). In a further embodiment, the activated ester is a vinyl ester of bromoacetic acid. Other activated esters of 2-haloacetic acid such as isopropenyl esters ($R_6$=$CH_3$), oxime esters, trichloroethyl or trifluoroethyl esters are known to those of skill in the art and are encompassed herein.

It is an advantage of the processes described herein that conversion of the rapamycin to the acylated rapamycin (VII) may be performed in a near quantitative yield. Desirably, the acylated rapamycin (VII) may be prepared in greater than a 95%, 96%, 97%, 98%, or 99% yield.

A variety of lipases can be utilized. In one embodiment, the lipase is a microbial lipase, i.e., a lipase with microbial origin which catalyzes the hydrolysis and formation of ester bonds. Microbial lipases include, for example, *Candida antarctica, Candida rugosa, Mucor miehei, Pseudomonas cepacia, Pseudomonas fluorescens, Rhizopus delemar,* and *Aspergillus niger*. However, the lipase selected for use herein need not be directly isolated and purified from the original source, but can be prepared synthetically or recombinantly, or through other suitable means. A variety of these enzymes are available from some commercial sources, further, these enzyme preparations can be used as crude, partially purified, purified or immobilized from different microbial origin under different trade names by various suppliers.

In one embodiment, the lipase from *Candida antarctica*, type B is utilized. *C. antarctica* lipase is commercially available, e.g., under the product designation Novo SP43™, Novozym 43™ (Novo Nordisk), or Chirazyme L-2™ (Roche Molecular Biochemicals and BioCatalytics). In another embodiment, the lipase from *Pseudomonas cepacia* is used. *Pseudomonas cepacia* is commercially available, e.g., under the product designation lipase PS (Amano Enzymes, Inc). Desirably, the enzyme is used as its immobilized form. In one embodiment, the immobilized lipase is lipase PS-C "Amano" II™ or lipase PS-C "Amano" I™ (Amano Enzymes, Inc.). In another embodiment, the immobilized lipase is lipase PS-D "Amano" I™ (Amano Enzymes, Inc.).

The lipase is used in an effective catalytic amount, i.e., an amount which effectively catalyzes the acylation at a reasonable rate. Those skilled in the art will appreciate that the enzyme can be used in an amount of about 20 to about 800 wt % (relative to the amount of the rapamycin or FK506/FK520). In one embodiment, the enzyme is used in an amount of about 25 to about 500 wt %. In another embodiment, the enzyme is used in an amount of about 50 to about 250 wt %. In a further embodiment, the enzyme is used in an amount of about 75 to about 150 wt %.

The reaction is typically carried out in an organic solvent. Suitable solvents include, but are not limited to, toluene, tert-butyl methyl ether (TBME), ethyl ether, tetrahydrofuran (THF), acetonitrile (MeCN), methylene chloride ($CH_2Cl_2$), chloroform ($CHCl_3$), di-isopropyl ether ($^iPr_2O$), hexane, dioxane, or mixtures including these solvents. In one embodiment, TBME is used. It will be appreciated by those skilled in the art that the solvent is used in an amount which can effectively dissolve all or part of starting rapamycin at the beginning and allows the reaction to proceed at a reasonable rate. For example, a solvent, such as TBME, can be used in an amount of at least 4 wt volume (i.e., a volume that is in an excess of 4 times (4×) the amount of rapamycin) to about 10 wt volume. In one example, a solvent can be used in an amount of about 5 to 8 wt volume, i.e., a volume that is in an excess of 5 to 8 times the amount of rapamycin.

TBME may contain residual water (e.g., about 0.05%) which could decompose the rapamycin compound. In order to minimize this side-reaction, a low amount of moisture is maintained in the reaction system. In one embodiment, anhydrous TBME is used with a standard commercial preparation of the lipase catalyst. In another embodiment, moisture can be controlled through adjusting the amount of water present in the lipase solution by adding a drying agent. In yet another embodiment, a molecular sieve can be used to control the moisture. Since a molecular sieve will slow the reaction, more enzyme may be added to compensate, or a longer reaction time can be used. In one embodiment, a 5 Å molecular sieve is used. However, other sieve sizes including, but not limited to, 4 Å and 3 Å, can be readily utilized. Suitable molecular sieves are available from a variety of commercial sources. In still another embodiment, drying agents such as $MgSO_4$, $Na_2SO_4$, among others, can be used to control the moisture content.

The acylation reaction is conducted at a temperature low enough to reduce the formation of unwanted by-products, but not so low as to require an unreasonably long reaction time. In one embodiment, the acylation is carried out at from about 20 to about 55° C. In another embodiment, the acylation reaction is carried out at about 25 to 50° C. In a further embodiment, the acylation reaction is carried out at about 35 to 45° C.

In one embodiment, the acylation is carried out by combining rapamycin, vinyl bromoacetate, and lipase PS-C "Amano" II™ (100% w/w as rapamycin) in anhydrous TBME. The mixture is heated under nitrogen at 40° C. for about 8 hours or until the rapamycin starting material disappears as monitored by thin layer chromatography (TLC) or HPLC. After removing enzyme by filtration, rapamycin 42-bromoacetate was obtained in nearly quantitative yield.

Once the ester linker is introduced, the next step includes attachment of the PEG molecule to this activated rapamycin acetate (VII). The pegylation was accomplished by reacting (VII) with a methoxy polyethylene derivative having general formula $HX-(CH_2CH_2O)_n-CH_3$ (B) wherein X and n are defined above, in an organic solvent in the presence of a non-nucleophilic base.

As used herein, the term "non-nucleophilic base" refers to a chemical compound that functions as a base with no nucleophilicity. Desirably, the non-nucleophilic base does not react with the other compounds and reagents of the pegylation. A variety of non-nucleophilic bases are known to those of skill in the art. See, e.g., Richard C. Larock, in "Comprehensive Organic Transformation", $2^{nd}$ edition, 1999. In one embodiment, the non-nucleophilic base is a tertiary amine. In one example, the tertiary amine is an aliphatic amine. In another example, the tertiary amine is an aromatic amine. In a further example, the tertiary amine is a trialkylamine such as triethylamine or diisopropylethylamine.

Suitable solvents useful in the pegylation include, but are not limited to, THF, MeCN, $CH_2Cl_2$, $CHCl_3$, dioxane, dimethylformamide (DMF) or mixtures including these solvents. In one embodiment, MeCN is the solvent.

The PEG-rapamycin conjugate can be isolated using procedures well known to those of skill in the art including precipitation, extraction, filtration, among others.

Thus, in one embodiment, rapamycin 42-bromoacetate and mPEG thiol (MW~5000) was treated with diisopropylethylamine in acetonitrile for a certain period of time. By doing so, the desired PEG-rapamycin conjugate (I) may be obtained in excellent yield after a simple precipitation by adding isopropanol to reaction mixture.

In another embodiment, a process is provided for preparing a water soluble PEG-Everolimus (42-O-(2-hydroxy)ethyl rapamycin, RAD001) conjugate represented by the formula (II) through a two-step sequence as outlined in Scheme 3. The PEG-everolimus conjugate (II) may be prepared in a similar fashion as described for PEG-rapamycin conjugate (I). In summary, the reaction is performed via intermediate (VIII) which is available via a lipase-catalyzed acylation with an acylating agent of formula (A). Compound (VIII) is then reacted with a methoxypolyethylene derivative of formula (B) in the presence of a non-nucleophilic base in an organic solvent described above. In one example, the non-nucleophilic base is a trialkylamine. In another example, the organic solvent is acetonitrile. Compound II is thereby prepared in excellent yields and high purities with no need for further purification.

Scheme 3

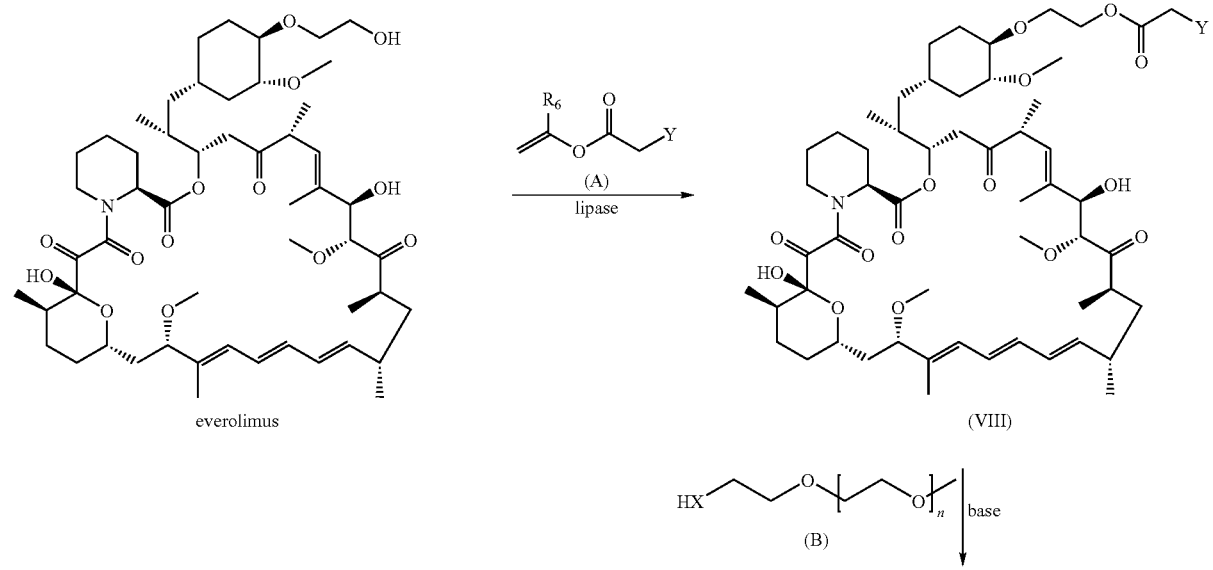

-continued

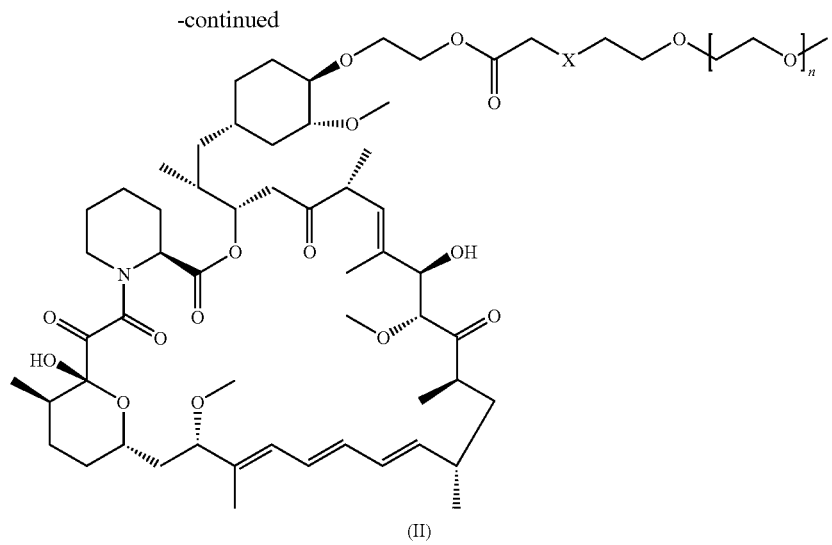

(II)

In another embodiment, a process is provided for preparing a water soluble PEG-CCI-779 conjugate represented by the formula (III), (IV), or a combination thereof through a similar two-step sequence. See, Scheme 4. One or both of the OH groups in the ester side chain at the 42-position of the CCI-779 molecule may be acylated with an acylating agent of formula (A) catalyzed by a lipase, as described in Scheme 3. The ratio of mono-acylated product (IX) and bis-acylated product (X) can be altered by the modification of the amount of lipase, amount of vinyl ester (A), reaction time, and temperature. Further, the compounds of formulas (IX) and (X) can be respectively separated from the mixture using chromatography. Compounds (IX) and (X) may then separately be used to prepare the corresponding PEG-CCI-779 conjugates (III) and (IV). Alternatively, compounds (IX) and (X) may be retained as a mixture, which mixture is used to prepare the corresponding PEG-CCI-779 conjugates (III) and (IV).

The preparation of PEG-conjugates (III) and (IV) was performed by reacting compounds (IX) and (X) with a methoxy-polyethylene derivative of formula (B) in the presence of a non-nucleophilic base described above in an organic solvent described above. In one example, the non-nucleophilic base is a trialkylamine. In another example, the organic solvent is acetonitrile. By doing so, conjugates (III) and (IV) may be prepared in excellent yields and with high purities, with no further purification step needed, respectively.

Scheme 4

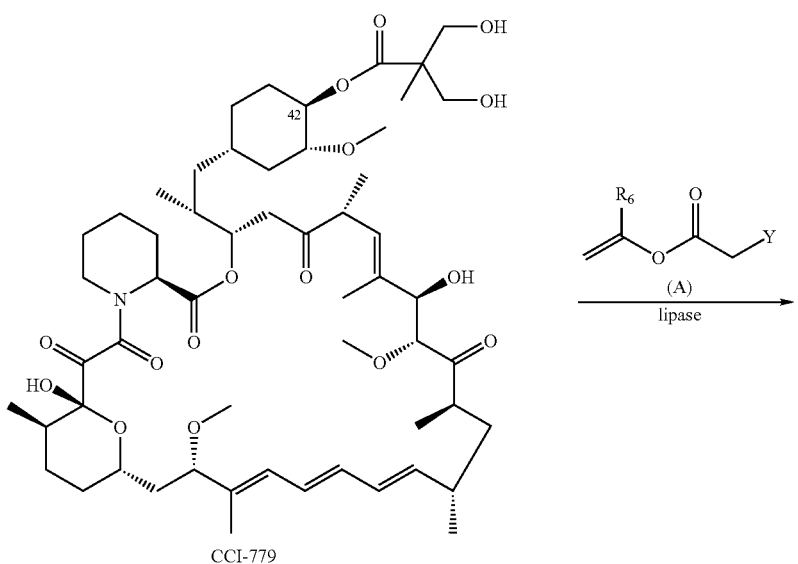

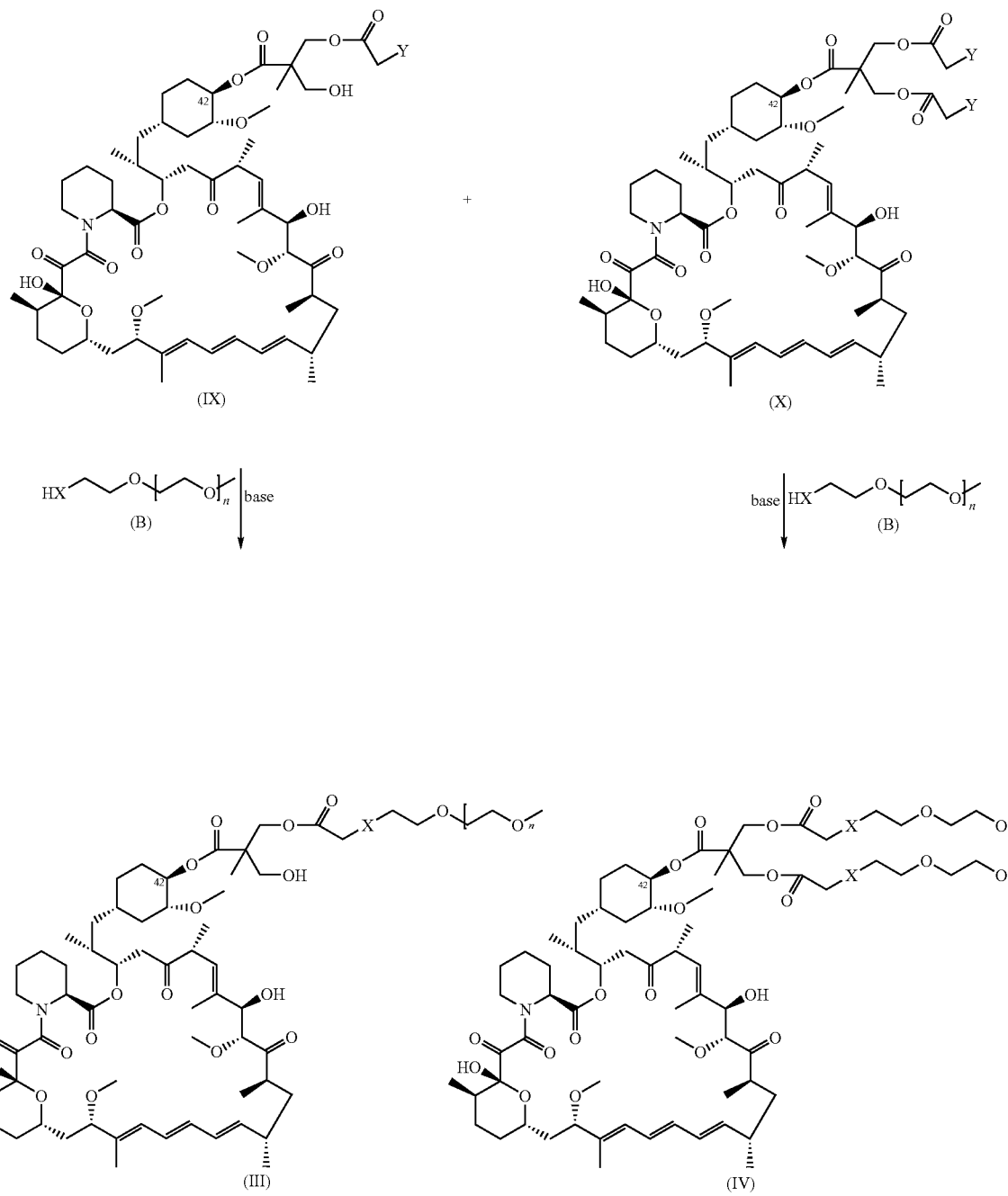

In still another embodiment, a process is provided for separately preparing water soluble PEG-tacrolimus and PEG-ascomycin conjugate represented by the formula (V) and (VI). As described in Scheme 5, the respective 32-esterifed intermediate (XI) can be obtained by acylating tacrolimus (FK506) or ascolimus (FK520) with an acylating agent of formula (A) in the presence of a lipase with excellent yield in a regiospecific fashion. Subsequent treatment of (XI) with a methoxypolyethylene derivative of formula (B) in the presence of a non-nucleophilic base described above in an organic solvent described above gave PEG-tacrolimus conjugate of formula (V) or PEG-ascolimus conjugate of formula (VI), with excellent yield and high purity, respectively. In one example, the non-nucleophilic base is a trialkylamine. In another example, the organic solvent is acetonitrile.

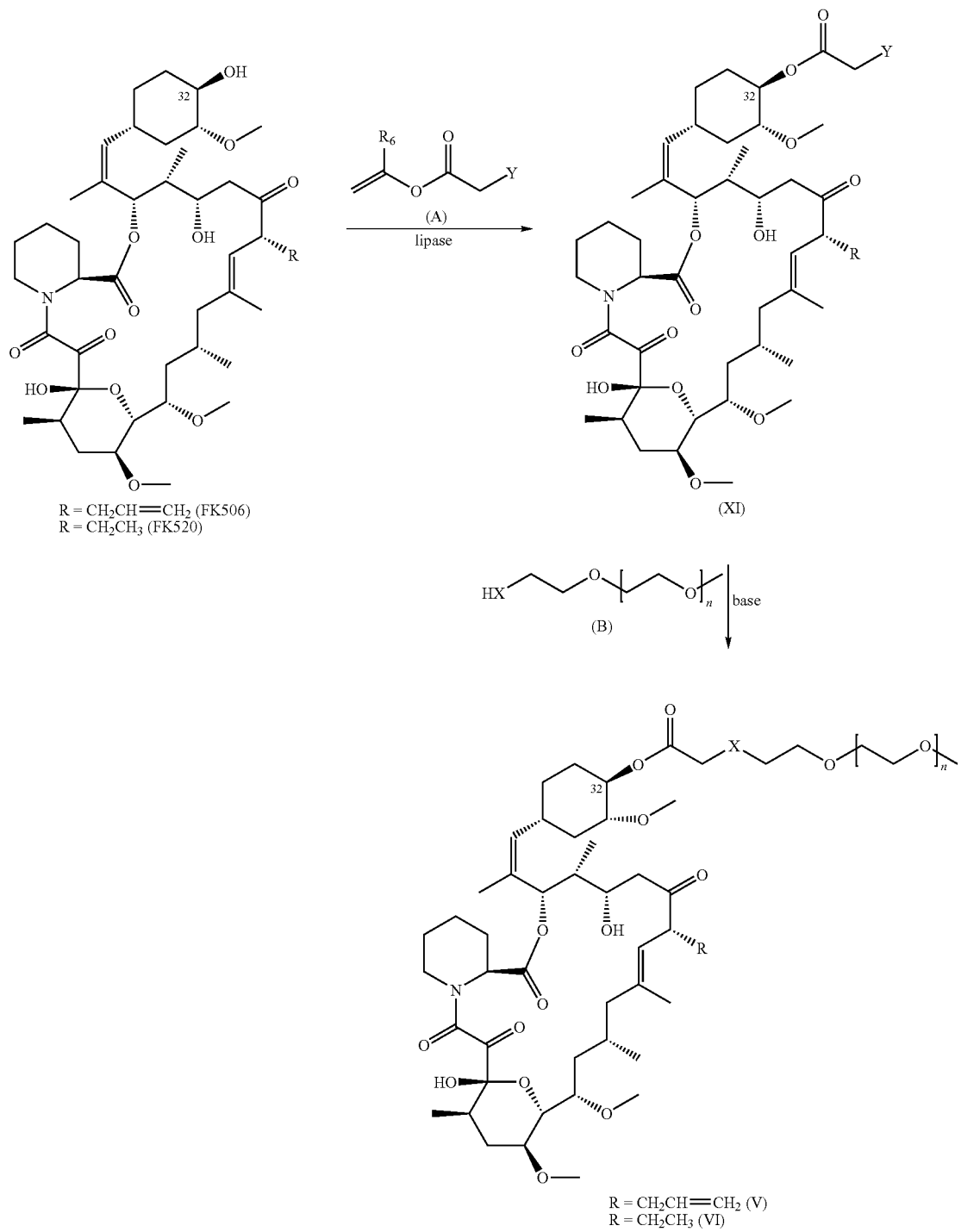

Scheme 5

The routes described herein provide several distinct advantages over the synthetic methodology published in U.S. Pat. Nos. 5,955,457; 6,331,547; 5,780,462; and 6,432,973 and International Patent Publication No. WO 99/03860. These advantages include ease of processing with no requirement of extra purification steps and higher overall yield. This is accomplished by using lipase as a catalyst to regiospecifically introduce the ester linker. The higher yield is also attributed to the use of an organic base, such as trialkylamine, in the subsequent conjugate reaction, instead of using an inorganic base, such as sodium bicarbonate, which decomposes the starting material and product. For example, the synthetic route described in U.S. Pat. No. 5,955,457 provides 42-pegylated rapamycin in less than 50% yield after two HPLC purifications, whereas the process described herein furnishes the product in nearly quantitative yield without the need of purification.
EXAMPLES
The following examples are illustrative only and are not intended to be a limitation on the present invention.
Example 1
Preparation of PEG-Rapamycin Conjugate (I) through Rapamycin 42-bromoacetate (VII)
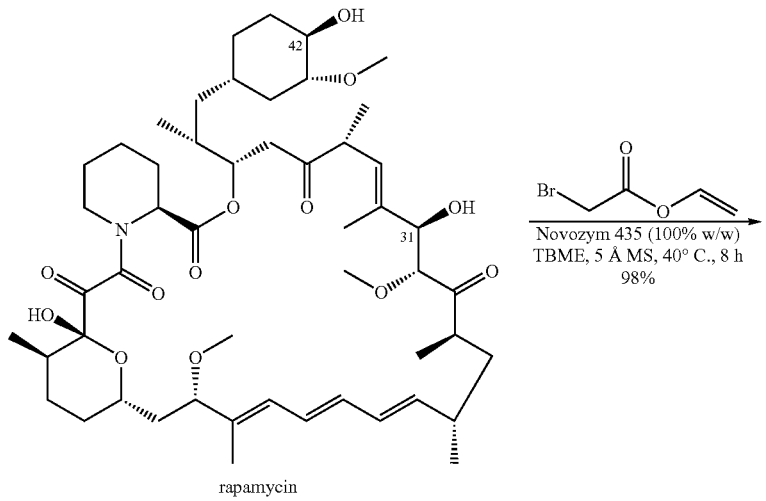
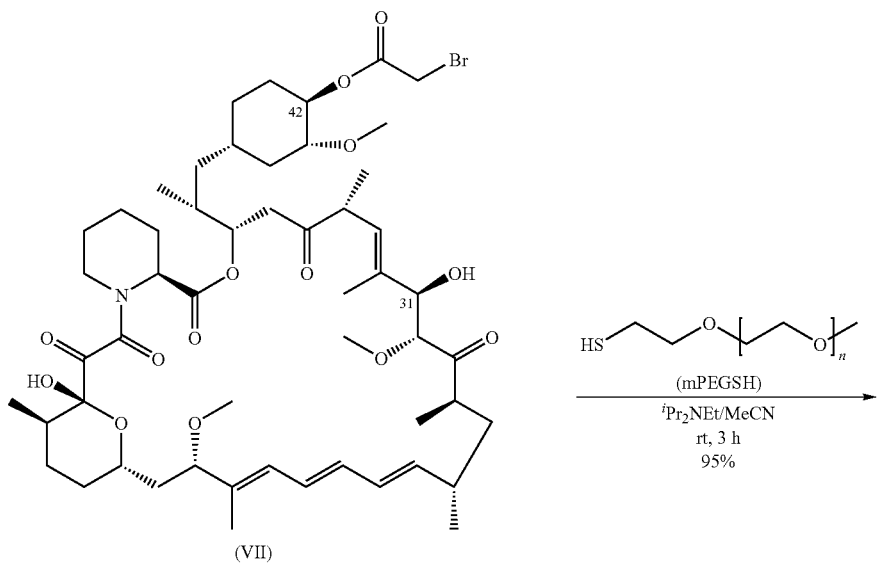

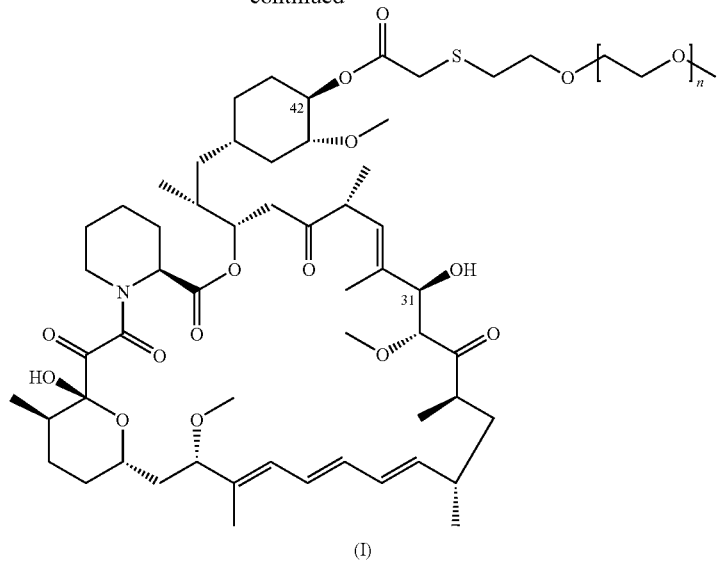

(I)

A. Preparation of Rapamycin 42-bromoacetate (VII)

A mixture of rapamycin (914 mg, 1 mmol), vinyl bromoacetate (660 mg, 4 mmol), 5 Å molecular sieves (100 mg) and Novozym 435™ lipase (1.0 g) in anhydrous t-butyl methyl ether (TBME) (8 mL) was heated under $N_2$ at 40° C. for 8 hours. The enzyme was removed by filtration and washed with TBME. The mixture was concentrated and precipitated into hexane. The rapamycin 42-bromoacetate (VII) was collected by filtration and dried in vacuo. Yield: 1.01 g (98%). MS (ESI) m/e 1035 (M⁻)

B. Preparation of PEG-Rapamycin Conjugate (I)

To a solution of mPEGSH (500 mg, MW=5000) in MeCN (1.5 mL) was added diisopropylethylamine (17 mg), followed by rapamycin 42-bromoacetate (VII) (95 mg). The mixture was then stirred at room temperature for 3 hours. 2-propanol (18 mL) was added and the mixture was cooled to 10-15° C. and held for 30 minutes. The precipitated pegylated rapamycin was collected by filtration and dried in vacuo.

Yield: 550 mg (95%). $^1$H NMR (400 MHz, $CDCl_3$): δ 2.84 (t, 2H, S—$CH_2$—$CH_2$), 3.27 (s, 2H, CO—$CH_2$—S), 3.36 (s, 3H, —$OCH_3$), 4.69 (m, 1H, H-42); MS (MALDI/TOF) m/z 5877.47 (average MW).

Example 2

Preparation of PEG-everolimus Conjugate (II) Through Everolimus 42-bromoacetate (VIII)

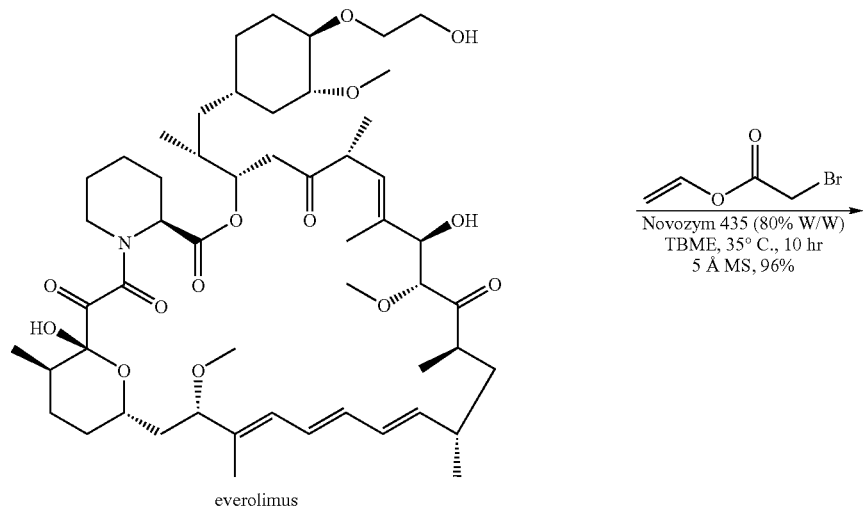

everolimus

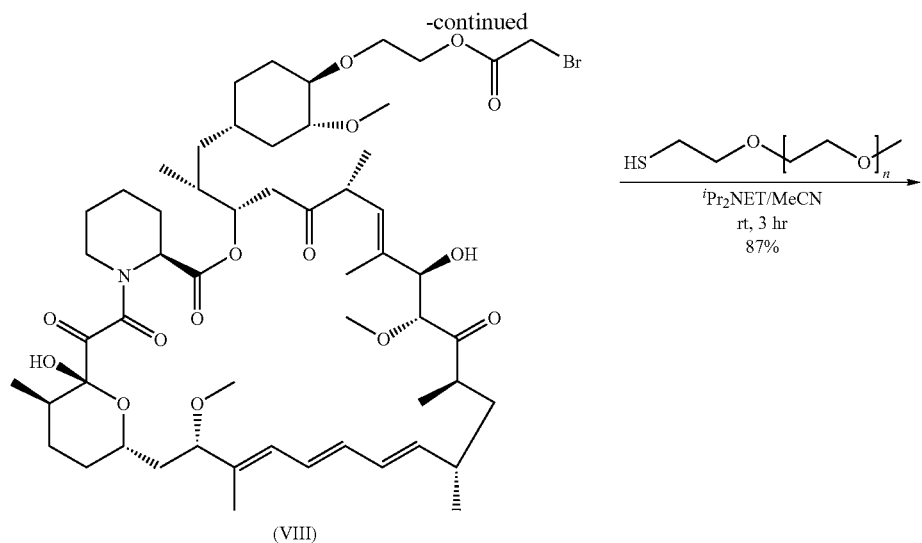

(VIII)

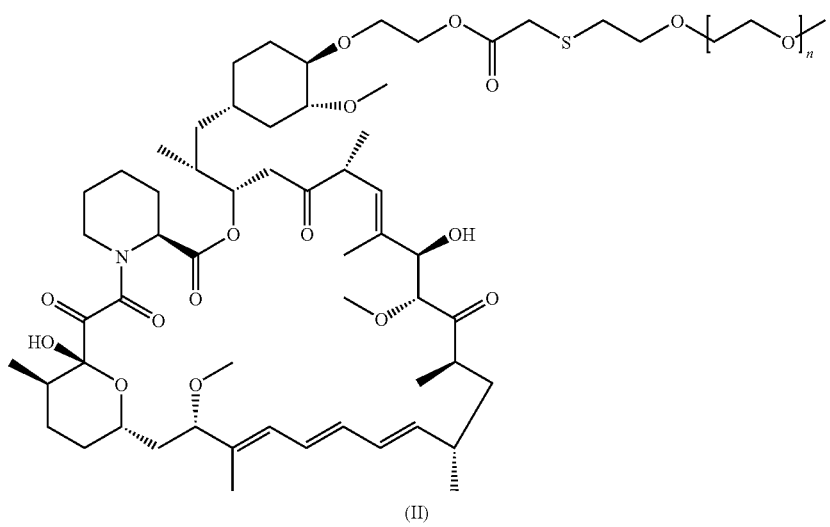

(II)

A. Preparation of Everolimus 42-bromoacetate (VIII)

A mixture of everolimus (250 mg, 0.26 mmol), vinyl bromoacetate (165 mg, 1 mmol), 5 Å molecule sieves (20 mg), and Novozym 435™ lipase (200 mg) in anhydrous t-butyl methyl ether (TBME) (3 mL) was heated under $N_2$ at 35° C. for 10 hours. The enzyme was removed by filtration and washed with TBME. The mixture was concentrated and triturated with hexane. The everolimus 42-bromoacetate (VIII) was collected by filtration and dried in vacuo. Yield: 275 mg (96%). MS (ESI) m/e 1078 (M⁻)

B. Preparation of PEG-everolimus Conjugate (II)

To a solution of mPEGSH (500 mg, MW=5000) in MeCN (1.5 mL) was added diisopropylethylamine (18 mg), followed by everolimus 42-bromoacetate (VII) (110 mg). The mixture was then stirred at room temperature for 3 hours. 2-propanol (18 mL) was added over 10 minutes and the mixture was cooled to 10-15° C. and held for 30 minutes. The white powder was collected by filtration and dried in vacuo. Yield: 530 mg (87%).
Example 3
Preparation of CCI-779 mono-bromoacetate (IX) and CCI-779 bis-bromoacetate (X)
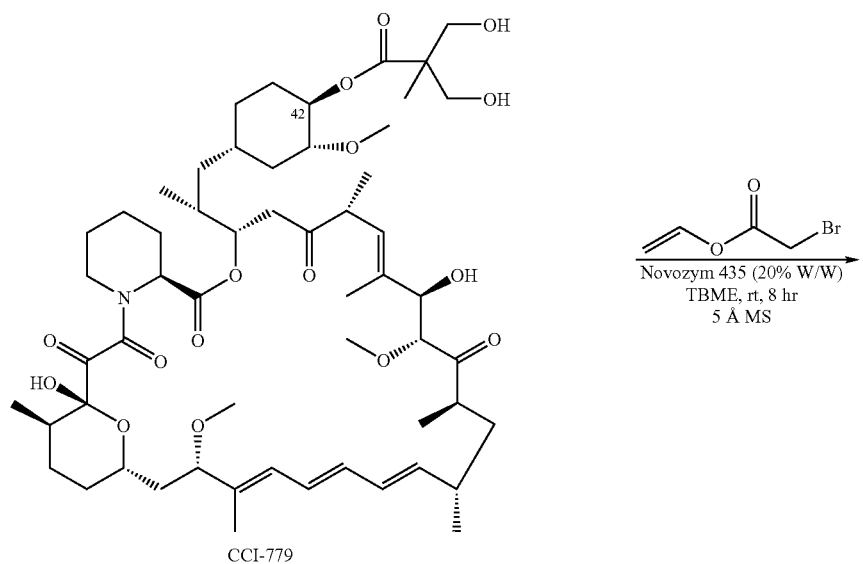
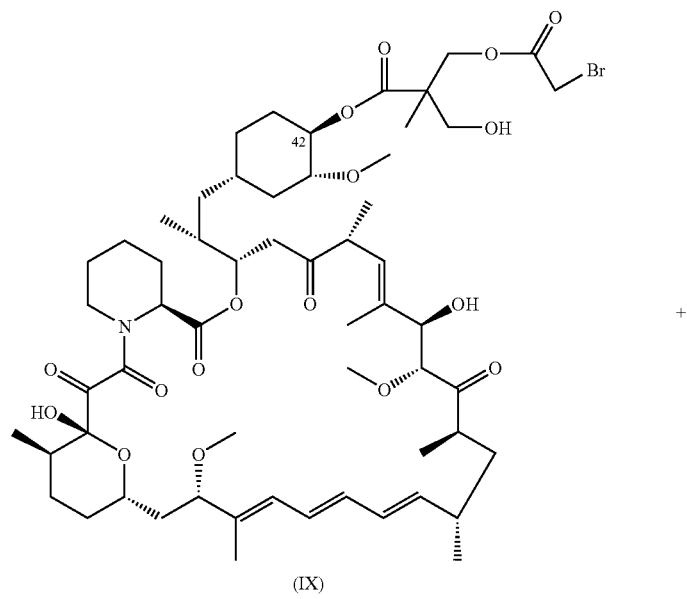

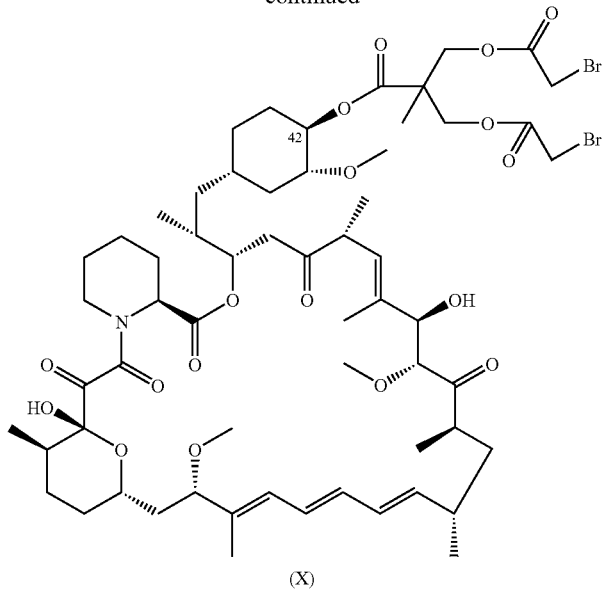

(X)

A mixture of CCI-779 (7.0 g, 6.8 mmol), vinyl bromoacetate (4.0 g, 24.24 mmol), 5 Å molecule sieves (2.0 g), and Novozym 435™ lipase (1.3 g) in anhydrous t-butyl methyl ether (TBME) (130 mL) was stirred at room temperature under $N_2$ for 8 hours. HPLC showed that the reaction mixture contained 64% mono-bromoacetate, 20% bis-bromoacetate and 12% CCI-779 starting material. The enzyme was removed by filtration and washed with TBME. The mixture was concentrated and purified by silica gel chromatography.

The less polar fraction contained bis-bromoacetate (X) and was collected (1.41 g). MS (ESI) m/e 1317 (M+45)⁻. The more polar fraction contained mono-bromoacetate (IX) (4.56 g), which was then isolated as a white powder. MS (ESI) m/e 1196 (M+45)⁻.

Example 4

Preparation of PEG-CC1779 Conjugate (III)

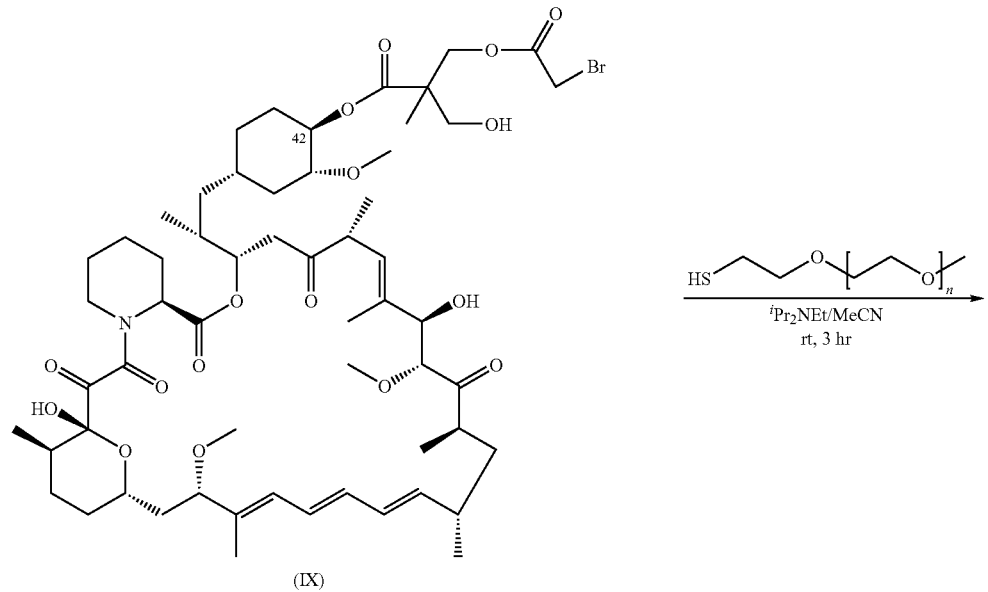

(IX)

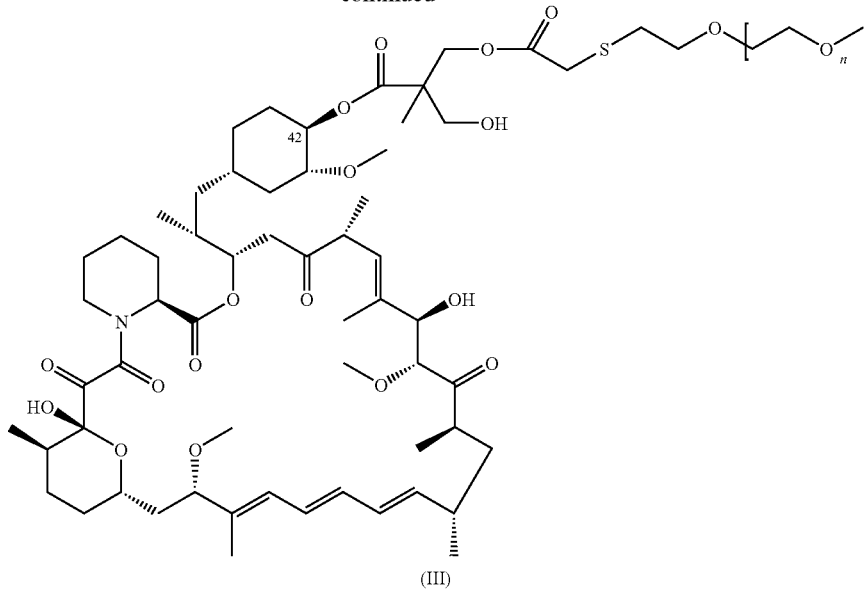

(III)

To a solution of mPEGSH (20.0 g, MW=5000) in MeCN (45 mL) was added diisopropylethylamine (722 mg, 5.6 mmol)) followed by CCI-779 mono bromoacetate (IX) (4.60 g, 4 mmol) as prepared in Example 3. The mixture was then stirred at room temperature for 4 hours. 2-propanol (540 mL) was added over 10 minutes and the mixture was cooled to 10-15° C. and held for 30 minutes. PEG-CCI-779 conjugate (III) as a white powder was collected by filtration and dried in vacuo. Yield: 20.3 g (83%).

Example 5

Preparation of PEG-CCI-779 Conjugate (IV)

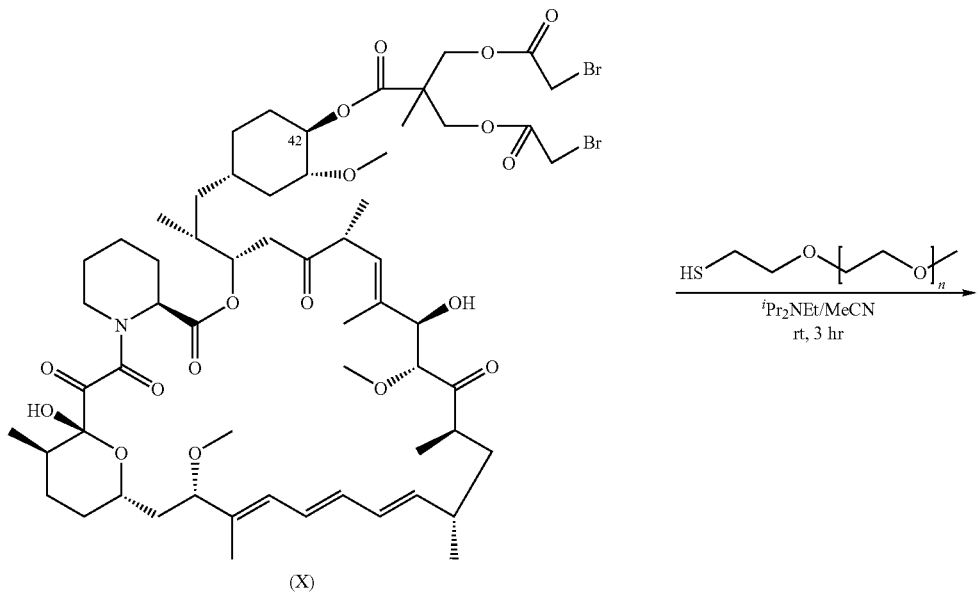

(X)

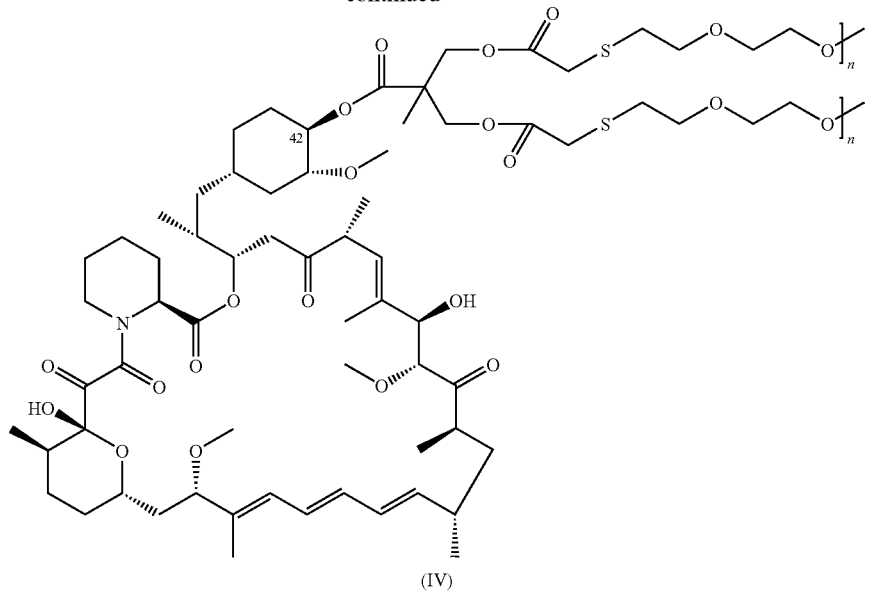

(IV)

To a solution of mPEGSH (3.0 g, MW=5000) in MeCN (9 mL) was added diisopropylethylamine (101 mg, 0.78 mmol), followed by CCI-779 bis bromoacetate (X) (414 mg, 0.32 mmol) as prepared in Example 3. The mixture was then stirred at room temperature for 4 hours. 2-propanol (108 mL) was added over 10 minutes and the mixture was cooled to 10-15° C. and held for 30 minutes. PEG-CCI779 conjugate (IV) as a white powder was collected and dried in vacuo. Yield: 3.25 g (96%).

Example 6

Preparation of Peg-tacrolimus Conjugate (V) Through Tacrolimus 32-bromoacetate (XI)

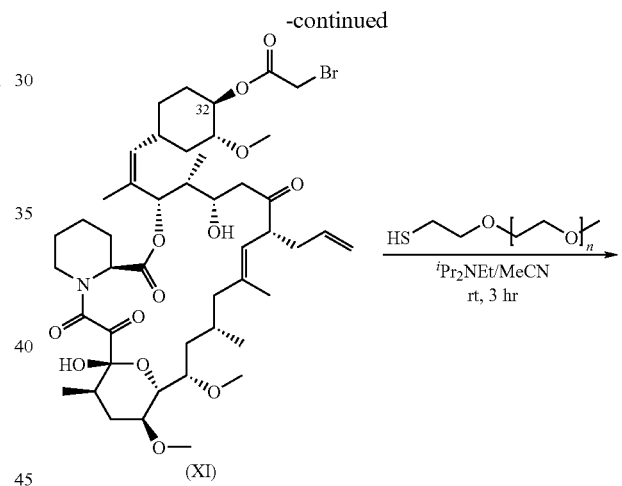

(XI)

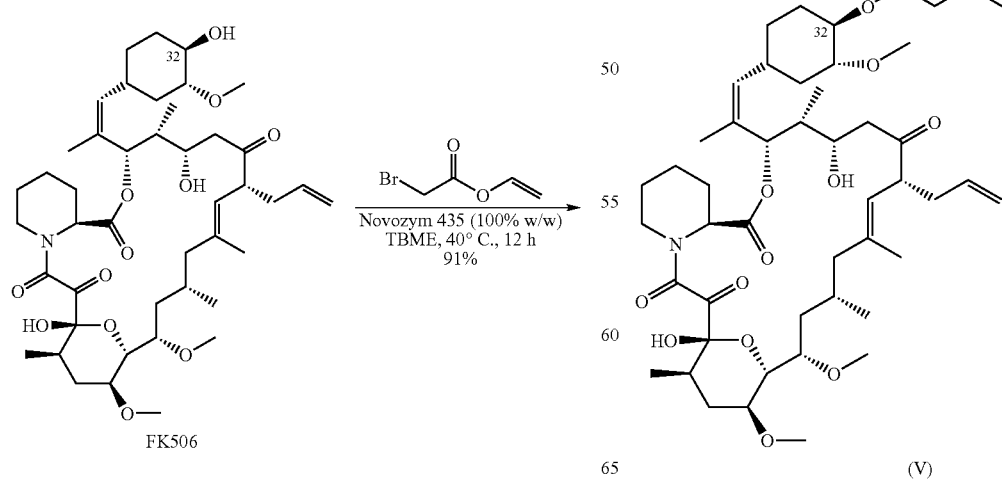

(V)

A. Preparation of Tacrolimus 32-Bromoacetate (XI)

A mixture of tacrolimus (10 mg), vinyl bromoacetate (20 mg) and the Novozym 435™ lipase (20 mg) in anhydrous t-butyl methyl ether (TBME) (0.2 mL) was heated under $N_2$ at 40° C. for 12 hours. The enzyme was removed by filtration and washed with TBME. The filtrate was passed through a silica gel pad and washed with hexane-acetone (3:1). The tacrolimus 32-bromoacetate was collected and dried in vacuo. Yield: 10.5 mg (91%). MS (ESI) m/e 924 (M⁻)

B. Preparation of PEG-tacrolimus Conjugate (V)

To a solution of mPEGSH (25 mg, MW=5000) in MeCN (0.1 mL) was added diisopropylethylamine (1 mg), followed by tacrolimus 32-bromoacetate (5 mg). The mixture was then stirred at room temperature for 3 hours. 2-propanol (1.5 mL) was added and the mixture was cooled to 10-15° C. and held for 30 minutes. The precipitated PEG-tacrolimus conjugate (V) was collected by filtration and dried in vacuo. Yield: 24 mg (80%).

All publications cited in this specification are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A process for preparing polyethylene glycol conjugates of a rapamycin immunosuppressive macrolide of the following structure:

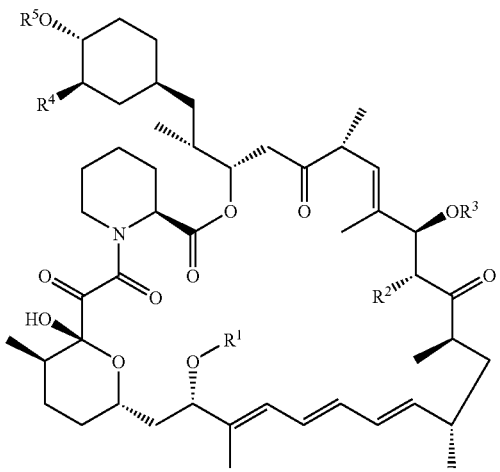

wherein:
R¹ is selected from the group consisting of H, and alkyl, alkenyl, aryl, and arylalkyl;
R² is selected from the group consisting of H, hydroxyl, and —O-alkyl;
R³ is selected from the group consisting of H, alkyl, alkenyl, aryl, arylalkyl, and —C(O)R³¹;
R³¹ is selected from the group consisting of H, alkyl, alkenyl, aryl, and arylalkyl;
R⁴ is selected from the group consisting of H, hydroxyl, and —O-alkyl;
R⁵ is selected from the group consisting of H, hydroxyalkyl, hydroxyalkenyl, hydroxyaryl, hydroxyaralkyl, and —C(O)R⁵¹; and
R⁵¹ is selected from the group consisting of hydroxyalkyl, hydroxyalkenyl, hydroxyaryl, and hydroxyaralkyl;

the process comprising:
(a) reacting an acylating agent with said rapamycin, said rapamycin being regiospecifically acylated at the 42-position;
(b) reacting the acylated macrolide with a methoxy poly (ethylene glycol) derivative or thiol-terminated poly (ethylene glycol) derivative in the presence of a base.

2. The process according to claim 1, wherein the immunosuppressive macrolide is 42-O-(2-hydroxy)ethyl rapamycin.

3. The process according to claim 1, wherein the immunosuppressive macrolide is CCI-779.

4. A process for preparing polyethylene glycol conjugates of immunosuppressive macrolides of the following structures:

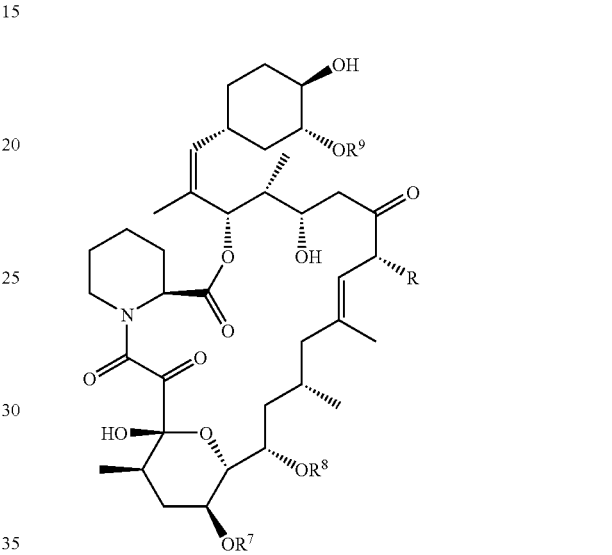

wherein:
R⁷, R⁸, R⁹ are independently H or alky;
R is ethyl or allyl; the process comprising:
(a) reacting an acylating agent with said immunosuppressive macrolides which are regiospecifically acylated at the 32-position; and
(b) reacting the acylated macrolide with a methoxy poly (ethylene glycol) derivative or thiol-terminated poly (ethylene glycol) derivative in the presence of a base.

5. The process according to claim 1, wherein said lipase is a microbial lipase from microorganisms comprising *Aspergillus niger, Candida antarctica, Candida rugosa, Mucor miehei, Pseudomonas cepacia, Pseudomonas fluorescens*, or *Rhizopus delemar*.

6. The process according to claim 1, wherein said lipase is from *Candida antarctica*.

7. The process according to claim 1, wherein said lipase is immobilized Novozym 435™ from *Candida antarctica* type B.

8. The process according to claim 1, wherein said lipase is lipase PS from *Pseudomonas cepacia*.

9. The process according to claim 1, wherein said lipase is immobilized lipase PS-C Amano II™ lipase or lipase PS-D Amano I™ lipase from *Pseudomonas cepacia*.

10. The process according to claim 1, wherein step (a) is performed at 20 to 70° C.

11. The process according to claim 10, wherein step (a) is performed at 40° C. in tert-butyl methyl ether, said acylating agent is vinyl bromoacetate, said lipase is the Novozym 435™ lipase, and further comprises 5 Å molecular sieves.

12. The process according to claim 1, wherein the acylating agent is vinyl bromoacetate.
13. The process according to claim 1, wherein said base is diisopropylethylamine.
14. A process for preparing a pegylated immunosuppressive macrolide selected from the group consisting of formula I, formula II, formula III, formula IV, formula V, and formula VI:
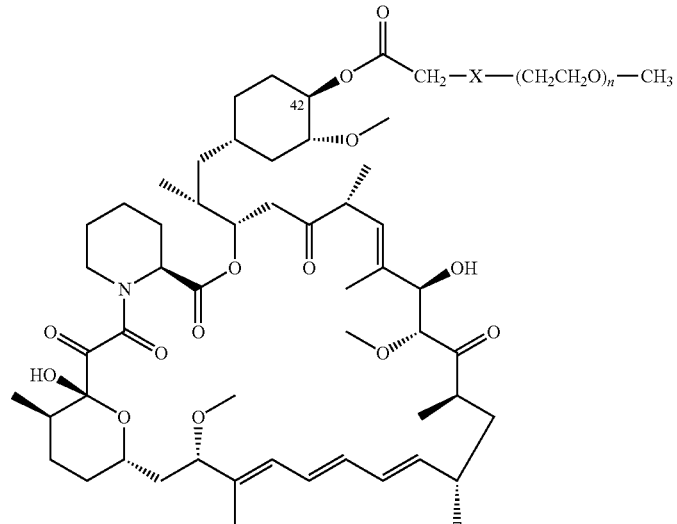
(I)
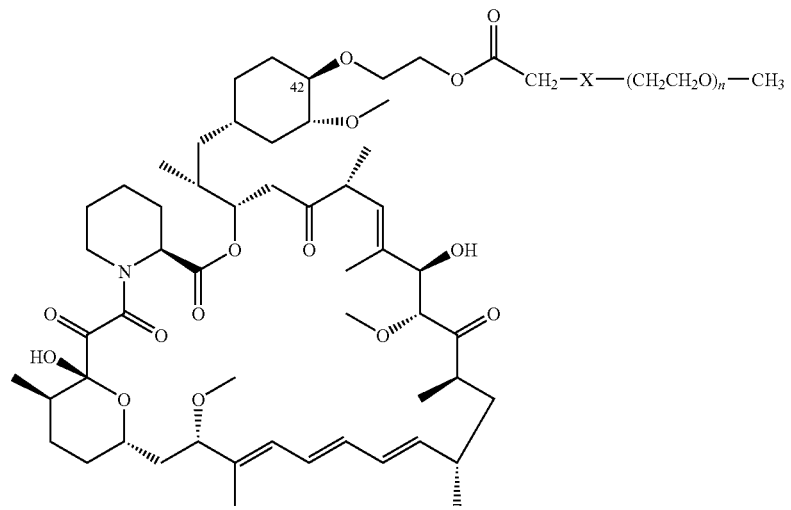
(II)

-continued
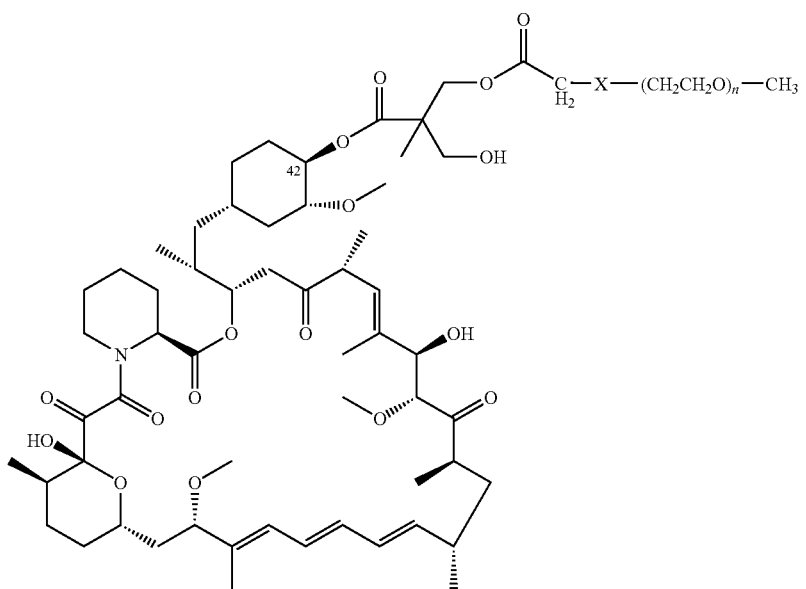
(III)
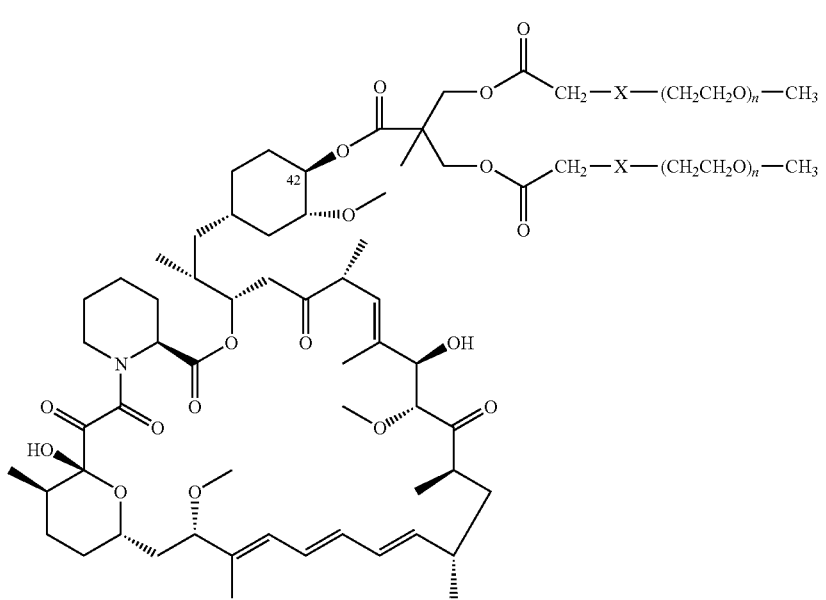
(IV)

-continued
(V)
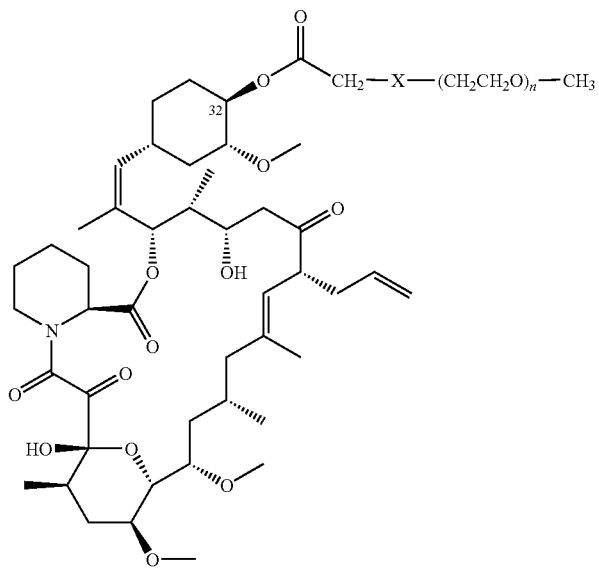
(VI)
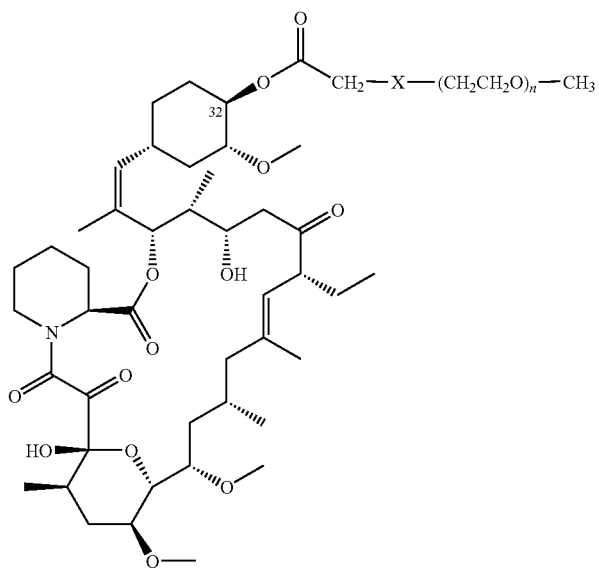
wherein:
n is an integer from 10 to 1000;
X is O or S;
said process comprising:
(a) reacting the macrolide with an acylating agent in the presence of a lipase to form an acylated macrolide, wherein said acylating agent is of the structure:
(A)
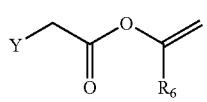
wherein:
$R^6$ is H or $CH_3$;
Y is a leaving group; and (b) reacting the acylated macrolide with a methoxy poly(ethylene glycol) derivative in the presence of a base, wherein said methoxy poly(ethylene glycol) derivative is of the structure:

wherein:

n is an integer from 10 to 1000; and

X is O or S.

15. The process according to claim 14, wherein Y is I, Br, or Cl.

16. The process according to claim 14, wherein said methoxy poly(ethylene glycol) derivative is a methoxy poly(ethylene glycol) thiol compound.

17. The process according to claim 16, wherein said methoxy poly(ethylene glycol) thiol has an average molecular weight of 400 to 30000.

18. The process according to claim 17, wherein said methoxy poly(ethylene glycol) thiol has an average molecular weight of 5000.

19. A process for preparing a pegylated rapamycin of the structure:

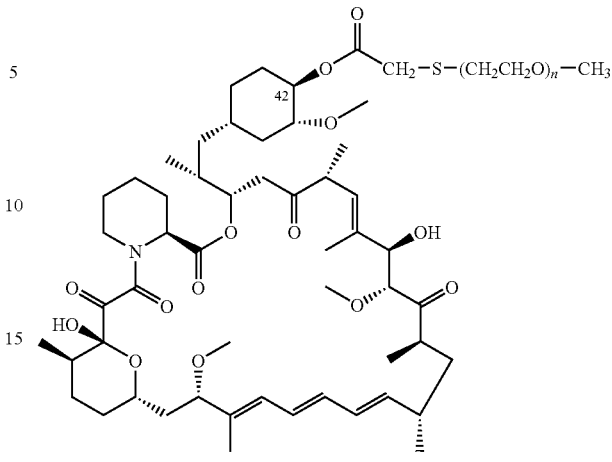

wherein:
n is 105-115;
wherein said process comprises:
(a) reacting rapamycin with vinyl bromoacetate in the presence of the Novozym 435™ lipase to form an acylated rapamycin; and
(b) reacting the acylated rapamycin with methoxy poly(ethylene glycol) thiol having an average molecular weight of 5000 in the presence of diisopropylethylamine.

20. A process for preparing a pegylated everolimus of the structure:

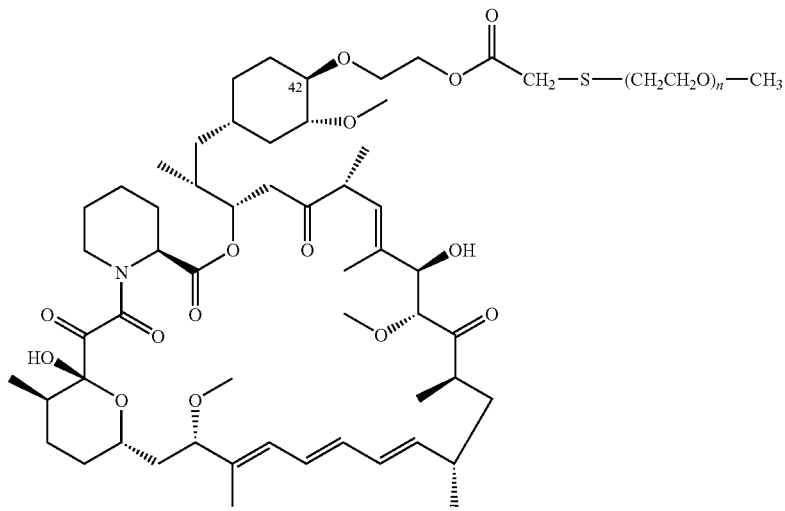

wherein, n is 105-115 and said process comprises:
(a) reacting everolimus with vinyl bromoacetate in the presence of the Novozym 435™ lipase to form an acylated everolimus; and
(b) reacting the acylated everolimus with methoxy poly(ethylene glycol) thiol having an average molecular weight of 5000 in the presence of diisopropylethylamine.

21. A process for preparing a pegylated CCI-779 of the structure:

wherein, n is 105-115 and said process comprises:
(a) reacting CCI-779 with vinyl bromoacetate in the presence of the Novozym 435™ lipase to form an monoacylated or bis-acylated CCI-779; and
(b) reacting the acylated CCI-779 with methoxy poly(ethylene glycol) thiol having an average molecular weight of 5000 in the presence of diisopropylethylamine.

22. A process for preparing a pegylated tacrolimus of the structure:

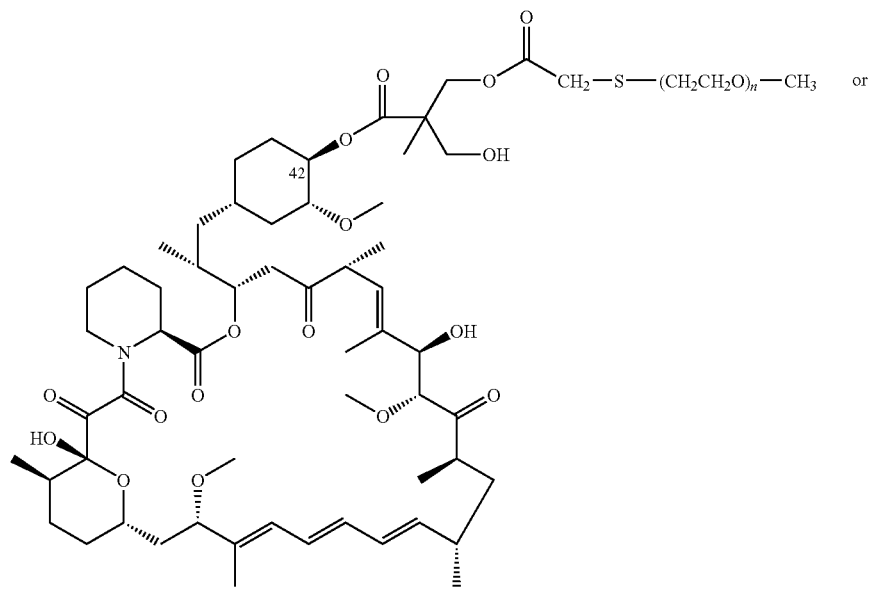

or

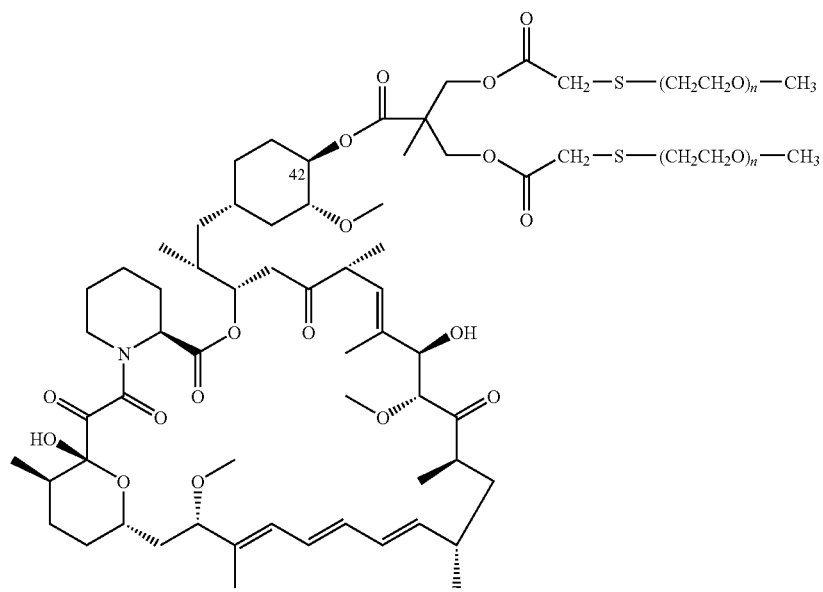

51

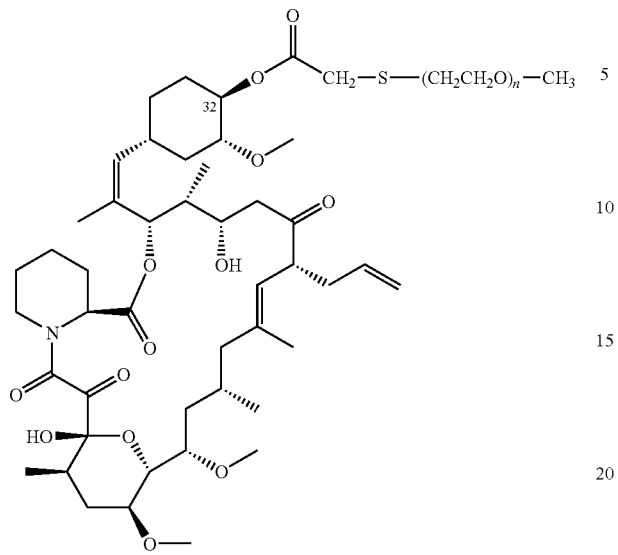

wherein, n is 105-115 and said process comprises:
  (a) reacting tacrolimus with vinyl bromoacetate in the presence of the Novozym 435™ lipase to form an acylated tacrolimus; and
  (b) reacting the acylated tacrolimus with methoxy poly(ethylene glycol) thiol having an average molecular weight of 5000 in the presence of diisopropylethylamine.

23. A process for preparing a pegylated tacrolimus of the structure:

52

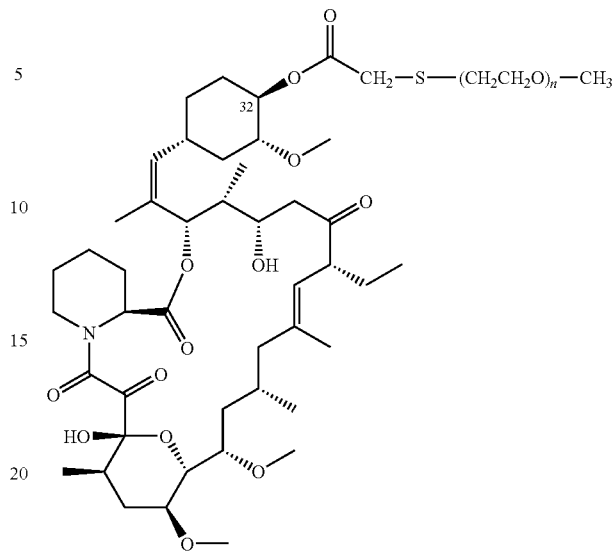

wherein, n is an integer from 105 to 115, and said process comprises:
  (a) reacting tacrolimus with vinyl bromoacetate in the presence of the Novozym 435™ lipase to form an acylated tacrolimus; and
  (b) reacting the acylated tacrolimus with methoxy poly(ethylene glycol) thiol having an average molecular weight of 5000 in the presence of diisopropylethylamine.

* * * * *